(12) United States Patent
Libman et al.

(10) Patent No.: US 9,804,104 B2
(45) Date of Patent: Oct. 31, 2017

(54) APPLYING RF ENERGY ACCORDING TO TIME VARIATIONS IN EM FEEDBACK

(71) Applicant: GOJI LTD., Hamilton (BM)

(72) Inventors: Avner Libman, Holon (IL); Hertzel Yehezkely, Rosh-HaAyin (IL); Sharon Hadad, Givataim (IL); Ram Elboim, Modiin (IL); Zalman Ibragimov, Rehovot (IL); Amit Rappel, Ofra (IL)

(73) Assignee: GOJI LIMITED, Hamilton (BM)

( * ) Notice: Subject to any disclaimer, the term of this patent is extended or adjusted under 35 U.S.C. 154(b) by 472 days.

(21) Appl. No.: 14/386,149

(22) PCT Filed: Mar. 14, 2013

(86) PCT No.: PCT/IB2013/001178
§ 371 (c)(1),
(2) Date: Sep. 18, 2014

(87) PCT Pub. No.: WO2013/140266
PCT Pub. Date: Sep. 26, 2013

(65) Prior Publication Data
US 2015/0070029 A1    Mar. 12, 2015

Related U.S. Application Data

(60) Provisional application No. 61/612,951, filed on Mar. 19, 2012.

(51) Int. Cl.
*G01N 22/00*     (2006.01)
*H05B 6/68*      (2006.01)
*H05B 6/70*      (2006.01)

(52) U.S. Cl.
CPC ............. *G01N 22/00* (2013.01); *H05B 6/686* (2013.01); *H05B 6/705* (2013.01); *Y02B 40/143* (2013.01)

(58) Field of Classification Search
CPC ........ G01N 22/00; H05B 6/686; H05B 6/705; Y02B 40/143
(Continued)

(56) References Cited

U.S. PATENT DOCUMENTS

| 4,434,342 A | 2/1984 | Schubring |
| 4,441,002 A | 4/1984 | Teich et al. |

(Continued)

FOREIGN PATENT DOCUMENTS

| DE | 19718399 | 11/1998 |
| DE | 102007003225 | 7/2008 |

(Continued)

OTHER PUBLICATIONS

Search report from International Patent Appl. No. PCT/IB2013/001178, mail date is Sep. 15, 2013.

(Continued)

*Primary Examiner* — Melissa Koval
*Assistant Examiner* — Courtney McDonnough
(74) *Attorney, Agent, or Firm* — Greenblum & Bernstein, P.L.C.

(57) ABSTRACT

An apparatus for applying RF energy to process an object may include at least one controller configured to receive EM feedback-related values from an energy application zone, each of the values being associated with a respective MSE. The controller may also be configured to identify a change in one or more of the EM feedback-related values within a period of time; adjust the RF energy application based on the change in the EM feedback-related values identified, and cause application of RF energy to the energy application zone.

15 Claims, 11 Drawing Sheets

(58) Field of Classification Search
USPC ......................................................... 324/637
See application file for complete search history.

(56) References Cited

U.S. PATENT DOCUMENTS

| | | | |
|---|---|---|---|
| 4,447,693 A | 5/1984 | Buck | |
| 4,541,729 A | 9/1985 | Schubring | |
| 4,841,111 A | 6/1989 | Kokkeler et al. | |
| 5,893,051 A | 4/1999 | Tomohiro | |
| 6,097,019 A | 8/2000 | Lewis et al. | |
| 6,299,921 B1 | 10/2001 | Loffler et al. | |
| 8,043,642 B2 | 10/2011 | Schonemann | |
| 8,178,142 B2 | 5/2012 | Greiner et al. | |
| 8,344,294 B2 | 1/2013 | Greiner et al. | |
| 8,492,686 B2 | 7/2013 | Bilchinsky et al. | |
| 8,653,482 B2 | 2/2014 | Ben-Shmuel | |
| 8,839,527 B2 | 9/2014 | Ben-Shmuel et al. | |
| 2008/0193614 A1 | 8/2008 | Greiner et al. | |
| 2009/0057302 A1 | 3/2009 | Ben-Shmuel et al. | |
| 2009/0061070 A1 | 3/2009 | Greiner et al. | |
| 2009/0274805 A1 | 11/2009 | Schonemann | |
| 2011/0198343 A1 | 8/2011 | Bilchinsky et al. | |
| 2012/0067872 A1* | 3/2012 | Libman | H05B 6/647 219/702 |
| 2012/0097665 A1 | 4/2012 | Bilchinsky et al. | |
| 2012/0111856 A1 | 5/2012 | Nobue et al. | |
| 2012/0122072 A1 | 5/2012 | Bilchinsky et al. | |
| 2012/0312801 A1 | 12/2012 | Bilchinsky et al. | |
| 2013/0048880 A1 | 2/2013 | Einziger et al. | |
| 2013/0048881 A1 | 2/2013 | Einziger et al. | |
| 2013/0062334 A1 | 3/2013 | Bilchinsky et al. | |
| 2013/0080098 A1 | 3/2013 | Hadad et al. | |
| 2013/0087545 A1 | 4/2013 | Bilchinsky et al. | |
| 2013/0142923 A1 | 6/2013 | Torres et al. | |
| 2013/0146590 A1 | 6/2013 | Einziger et al. | |
| 2013/0200065 A1 | 8/2013 | Libman et al. | |
| 2013/0200066 A1 | 8/2013 | Gelbart et al. | |
| 2013/0306626 A1* | 11/2013 | Torres | B65D 81/3446 219/635 |
| 2013/0306627 A1 | 11/2013 | Libman et al. | |
| 2014/0247060 A1 | 9/2014 | Ben Haim et al. | |
| 2014/0287100 A1 | 9/2014 | Libman | |

FOREIGN PATENT DOCUMENTS

| | | |
|---|---|---|
| EP | 0268329 | 5/1988 |
| EP | 1956301 | 8/2008 |
| EP | 2031306 | 3/2009 |
| WO | 2011/138688 | 11/2011 |
| WO | 2012/001523 | 1/2012 |
| WO | 2013/021280 | 2/2013 |
| WO | 2013/033330 | 3/2013 |

OTHER PUBLICATIONS

International Preliminary Report on Patentability and Written Opinion of the International Searching Authority in PCT/IB2011/001981, dated Jan. 8, 2013.
EPO Communication pursuant to Article 94(3) in EP 11767467.1, dated Mar. 24, 2014.
EPO Communication pursuant to Article 94(3) in EP 11767467.1, dated Oct. 29, 2013.
Abstract of U.S. Pat. No. 6299921 of Oct. 9, 2001.
Abstract of US 2009/0274805 of Nov. 5, 2009.
Abstract of US 20080193614 of Aug. 14, 2008.
Abstract of US 20090061070 of Mar. 5, 2009.

* cited by examiner

APPLYING RF ENERGY ACCORDING TO TIME VARIATIONS IN EM FEEDBACK

This application claims the benefit of priority to U.S. Provisional Patent Application No. 61/612,951, filed on Mar. 19, 2012, which is incorporated herein in its entirety.

TECHNICAL FIELD

This is an International Patent Application relating to a device and method for applying electromagnetic (EM) energy, and more particularly but not exclusively to controlling RF energy application based on variations in EM feedback received from an energy application zone.

BACKGROUND

EM waves have been used in various applications to supply energy to objects. In the case of radio frequency (RF) radiation for example, EM energy may be supplied using a magnetron, which is typically tuned to a single frequency for supplying EM energy only in that frequency. One example of a commonly used device for supplying EM energy is a microwave oven. Typical microwave ovens supply EM energy at or about a single frequency of 2.45 GHz.

SUMMARY OF A FEW EXEMPLARY ASPECTS OF THE DISCLOSURE

Some exemplary aspects of the disclosure include apparatuses and methods for applying EM energy to process an object in an energy application zone and more particularly for controlling the RF energy application based on changes in EM feedback-related values received from the energy application zone. EM feedback-related values received from the energy application zone may each be associated with a respective Modulation Space Element (MSE). As used hereinafter a Modulation Space Element (MSE) includes one or more controllable parameters that affect a field pattern excited in the energy application zone. An EM feedback-related value may be received/detected/measured (receiving may include calculation or evaluation on detected signals) during the application of RF energy at the respective MSE. A change within a time period may be detected or identified in the EM feedback related value. For example, a time difference (e.g., a derivative-e.g., discrete derivative or continuous derivative) of the EM feedback related value (e.g., a dissipation ratio (DR) value) at each MSE may be identified. RF energy application may be controlled based on the identified changes. In some embodiments, the RF energy application may be adjusted based on the changes identified in the EM feedback related value(s) at that MSE. For example, the RF energy application may be adjusted by determining an amount of energy to be applied at a particular MSE based on the changes identified in the EM feedback related value(s) at that MSE. For example, substantially low amount of RF energy may be applied at MSE associated with time derivative of the DR lower than a threshold. Optionally, energy may not be applied at MSE associated with time derivative of the DR lower than a threshold.

Some exemplary aspects of the invention may be directed to an apparatus for applying RF energy to process an object. The apparatus may include an energy application zone and one or more radiating elements. The apparatus may further include a controller configured to receive from the energy application zone EM feedback-related values, wherein each value is associated with a respective MSE and determine a time derivative for each EM feedback related value. The controller may further be configured to adjust RF energy application to be applied at two or more MSEs (e.g., by determining amounts of energy to be applied at each MSE) based on a comparison between the determined time derivatives and at least one threshold value and cause application of RF energy.

In some embodiments of the invention, the controller may be configured to receive a first set of EM feedback related values, from an energy application zone, associated with two or more MSEs and cause the application of a first amount of RF energy at the two or more MSEs based on the received EM feedback related values. The controller may further be configured to receive a second set of EM feedback related values from an energy application zone at the two or more MSEs and identify a change between the first and the second sets of EM feedback related values at each MSE. Based on the identified change. The controller may cause the application of a second amount of RF energy at the two or more MSEs.

Some exemplary aspects of the invention may be related to an apparatus and method for applying Radio Frequency (RF) energy to process an object, placed in an energy application zone. The apparatus may include at least one controller configured to receive a first type of electromagnetic (EM) feedback related values from an energy application zone, each of the values being associated with a respective Modulation Space Element (MSE), for example, DR(MSEi). The controller may identify a change in one or more EM feedback related values of the first type within a period of time and if the change is lower than a threshold the controller may receive a second type of electromagnetic (EM) feedback related values from an energy application zone, each of the values being associated with a respective Modulation Space Element (MSE), for example, Zin(MSEi). The controller may identify a change in one or more EM feedback related values of the second type within a period of time and adjust the RF energy application at two or more MSEs based on the identified change in the second type of EM feedback related values, associated with the two or more MSEs within the period of time. The controller may cause application of the RF energy, via for example, at least one radiating element.

Some additional exemplary aspects of the invention may be related to an apparatus and method for detecting at least one of a processing state of an object and a change in the processing state of the object, placed in an application zone. The apparatus may include at least one controller configured to receive electromagnetic (EM) feedback-related values from the energy application zone, each of the values being associated with a respective Modulation Space Element (MSE) included in a set of MSEs and identify a change in one or more of the EM feedback related values within a period of time. If the change has being identified the controller may select a sub-set of MSEs based on the change in the EM feedback related values identified and receive EM feedback-related values at the selected sub-set of MSEs. The controller may further detect the processing state of the object and/or the change in the processing state of the object by detecting the received EM feedback-related values at the selected subset of MSEs. The EM feedback-related values may be associated with the processing state of the object or the change in the processing state of the object. In some embodiments, if the change has not being identified the controller is further configured to replace the set of MSEs.

In some embodiments, the apparatus and method for detecting at least one of a processing state of an object and a change in the processing state of the object may include applying RF energy at a plurality of frequencies. The apparatus may include at least one controller configured to receive electromagnetic (EM) feedback-related values from the energy application zone, each of the values being associated with a respective frequency included in a band of frequencies and identify a change in one or more of the EM feedback related values within a period of time. If the change has being identified the controller may select a sub-band of frequencies based on the change in the EM feedback related values identified and receive EM feedback-related values at the selected sub-band of frequencies. The controller may further detect the processing state of the object and/or the change in the processing state of the object by detecting the received EM feedback-related values at the selected sub-band of frequencies. The EM feedback-related values may be associated with the processing state of the object and/or the change in the processing state of the object. In some embodiments, if the change has not being identified the controller is further configured to replace the band of frequencies.

The drawings and detailed description which follow contain numerous alternative examples consistent with the invention. A summary of every feature disclosed is beyond the object of this summary section. For a more detailed description of exemplary aspects of the invention, reference should be made to the drawings, detailed description, and claims, which are incorporated into this summary by reference.

DETAILED DESCRIPTION

Reference will now be made in detail to exemplary embodiments of the invention, examples of which are illustrated in the accompanying drawings. When appropriate, the same reference numbers are used throughout the drawings to refer to the same or like parts.

In one respect, disclosed embodiments may involve apparatus and methods for applying electromagnetic (EM) energy. The term EM energy, as used herein, includes energy deliverable by EM radiation in all or portions of the EM spectrum, including but not limited to, radio frequency (RF), infrared (IR), near infrared, visible light, ultraviolet, etc. In one particular example, applied EM energy may include RF energy with a wavelength in free space of 100 km to 1 mm, which corresponds to a frequency of 3 KHz to 300 GHz, respectively. In some other examples, the applied EM energy may fall within frequency bands between 500 MHz to 1500 MHz or between 700 MHz to 1200 MHz or between 800 MHz-1 GHz. Applying energy in the RF portion of the EM spectrum is referred herein as applying RF energy. Microwave and ultra high frequency (UHF) energy, for example, are both within the RF range. In some other examples, the applied EM energy may fall only within one or more industrial, scientific and medical (ISM) frequency bands, for example, between 433.05 and 434.79 MHz, between 902 and 928 MHz, between 2400 and 2500 MHz, and/or between 5725 and 5875 MHz. Even though examples of the invention are described herein in connection with the application of RF energy, these descriptions are provided to illustrate a few exemplary principles of the invention, and are not intended to limit the invention to any particular portion of the EM spectrum.

In some embodiments, the RF energy may be applied to process an object. An object is considered to be processed by RF energy if at least one physical or chemical property (e.g., temperature, pressure, humidity, density, color, taste, conductivity, dielectric properties, chemical composition, etc) at one or more portions of the object may change due to the exposure to RF energy. For example, at least a portion of a frozen object may be thawed, a chemical reaction may be initiated in at least a portion of a chemical solution, a portion of a food item may be cooked, heated etc.

Figure 1A:
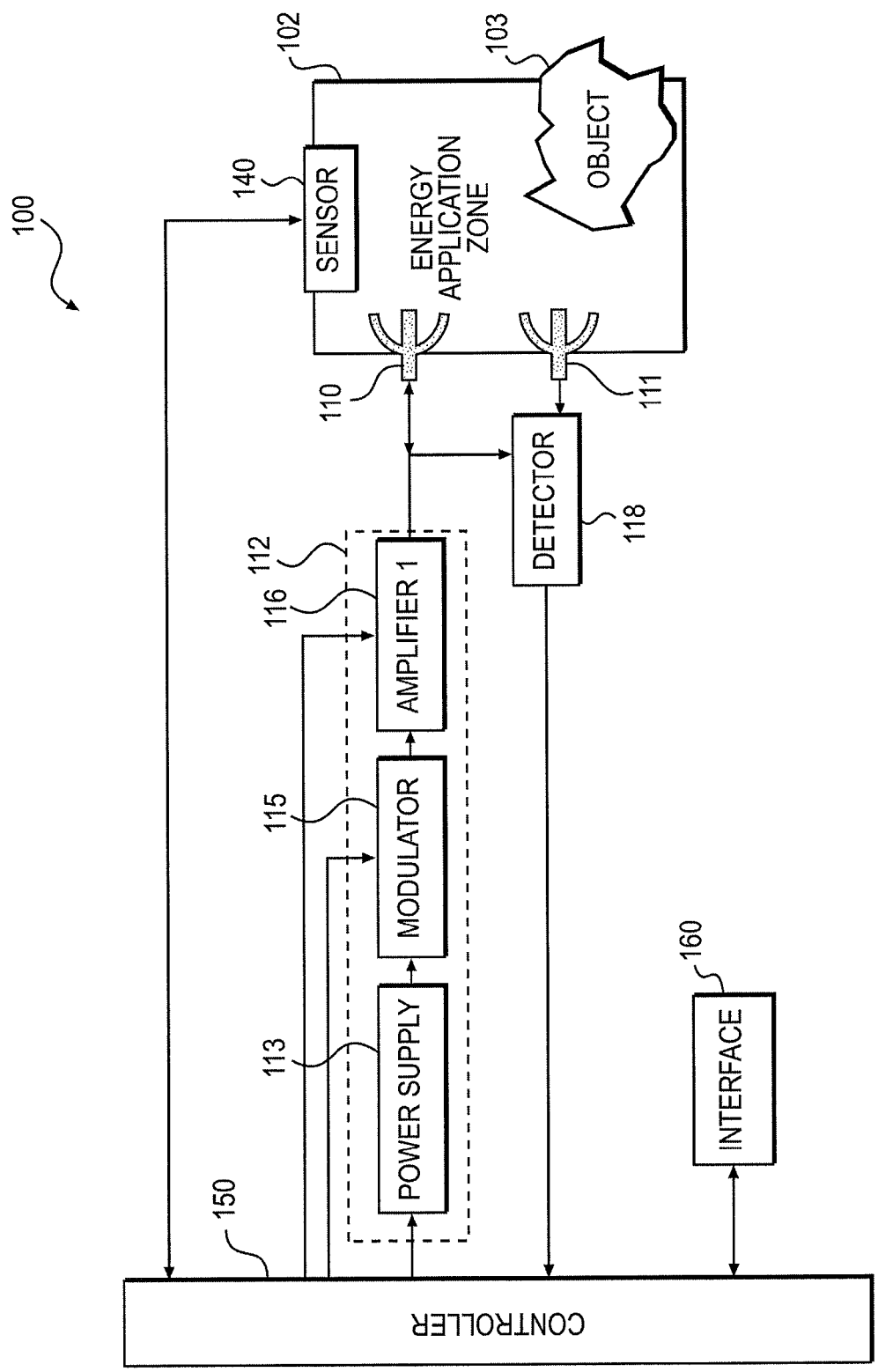
FIGS. 1A and 1B include diagrammatic representations of apparatuses for applying EM energy to an object, in accordance with some exemplary embodiments of the invention.
Figure 1B:
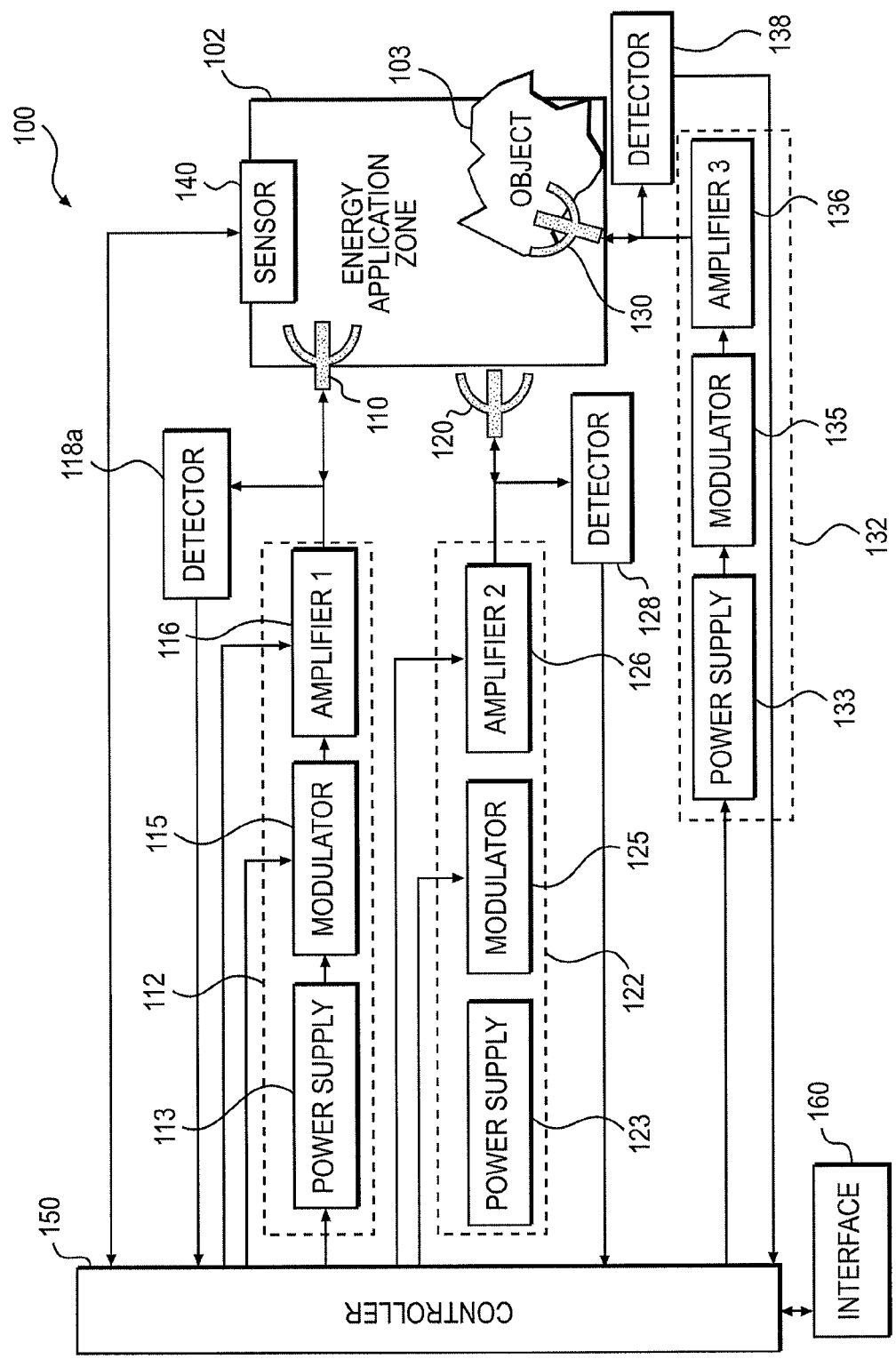

Referring now to FIGS. 1A and 1B that illustrates a diagrammatic representation of apparatuses for applying EM energy to process an object. Apparatus 100 may include an object 103 placed in an energy application zone 102 such that RF energy may be applied from radiating elements 110 and 111 and may be received back from energy application zone 102 at the radiating elements. Radiating elements 110 and 111 may be in communication with at least one detector 118 for detecting parameters indicative of RF energies that are applied from and/or received at radiating elements 110 and 111, also known as EM feedback-related values. As illustrated in FIG. 1A, radiating element 110 may receive RF energy from RF source 112. RF source 112 may include an RF power supply 113, a modulator 115 and an amplifier 116. RF source 112 may be controlled by a controller 150. Controller 150 may control each of power supply 113, modulator 115 and/or amplifier 116 based on the EM feedback received from detector 118. Controller 150 may be in communication with interface 160 for further communication with a user or a host apparatus (e.g., oven). Apparatus 100 may further include at least one sensor 140 for sensing a property of object 103 and/or zone 102. Sensor may be in communication with controller 150.

FIG. 1B illustrates apparatus 100 that further includes two RF sources 122 and 132 each for supplying RF energy to radiating elements 120 and 130 respectively. Each of RF sources 122 and 132 may include an RF power supply (power supply 123 or 133), a modulator (modulator 125 or 135) and an amplifier (amplifier 126 or 136) and may be controlled by controller 150 based on EM feedback received from detectors 128 and 138.

Figure 2:
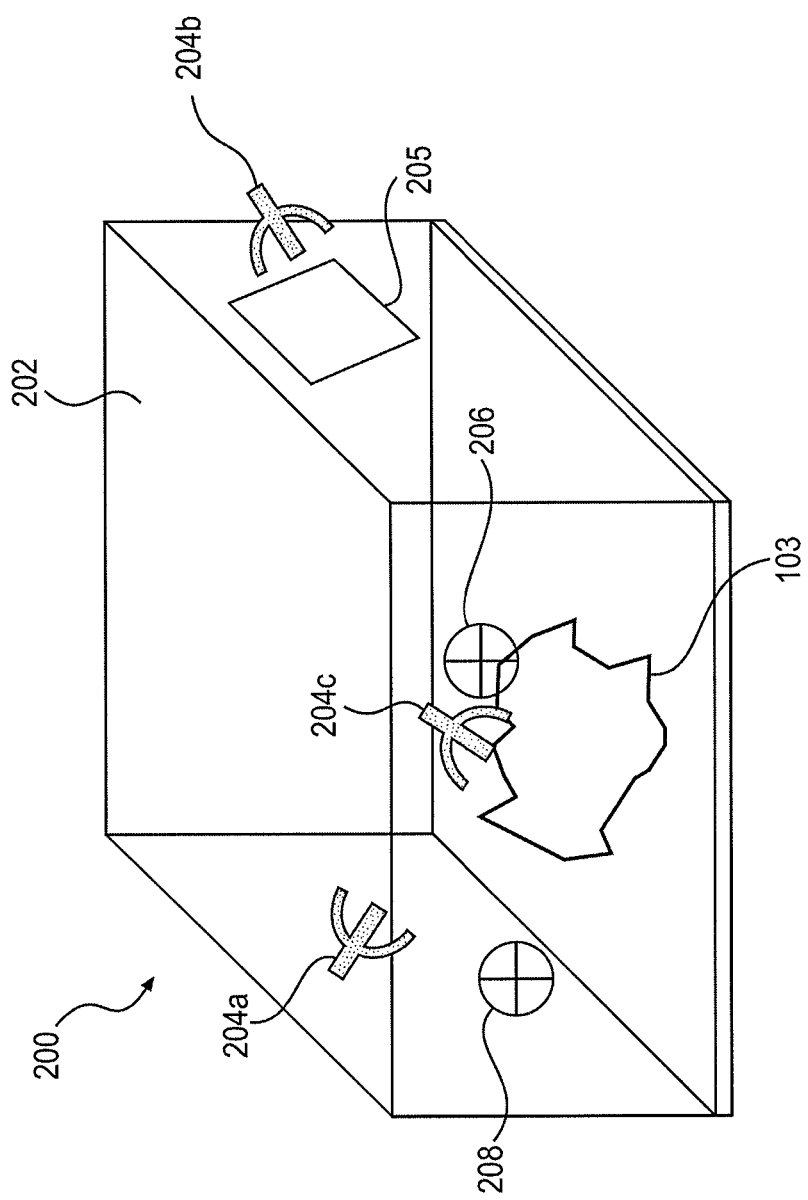
FIG. 2 include diagrammatic representations of cavity, in accordance with some exemplary embodiments of the invention.

In certain embodiments, RF energy may be applied to an object placed in an energy application zone, such as energy application zone 102, shown for example in FIGS. 1A and 1B. Energy application zone 102 may include any void, location, region, or area where EM energy may be applied. It may be hollow, or may be filled or partially filled with liquids, solids, gases, or combinations thereof. By way of example only, energy application zone 102 may include an interior of an enclosure, interior of a partial enclosure, open space, solid, or partial solid that allows existence, propagation, and/or resonance of EM waves. Zone 102 may include a conveyor belt or a rotating plate. At times, energy application zone 102 may be congruent with the object or a portion of the object (e.g., the object or a portion thereof, may define the energy application zone). For purposes of this disclosure, all such energy application zones may alternatively be referred to as cavities. Exemplary cavity is illustrated in FIG. 2.

In certain embodiments, EM energy may be applied to object 103 placed in the energy application zone. It is to be understood that an object is considered in or placed in the energy application zone if at least a portion of the object is located in the zone or if some portion of the object receives delivered EM radiation. A reference to an object (or object to be heated) to which RF is applied is not limited to a particular form. An object may include a liquid, semi-liquid, solid, semi-solid, or gas, depending upon the particular process with which the invention is utilized. The object may also include composites or mixtures of matter in differing phases. Thus, by way of non-limiting example, the term object encompasses such matter as food to be defrosted or cooked; clothes or other wet material to be dried; frozen organs to be thawed; chemicals to be reacted; fuel or other combustible material to be combusted; hydrated material to be dehydrated, gases to be expanded; liquids to be heated, boiled or vaporized, or any other material for which there is a desire to apply, even nominally, EM energy.

In some embodiments, a portion of EM energy supplied to energy application zone 102 may be absorbed by object 103. In some embodiments, another portion of the EM energy supplied or delivered to energy application zone 102 may be absorbed by various elements (e.g., food residue, particle residue, additional objects, structures associated with zone 102, or any other EM energy-absorbing materials found in zone 102 or associated with energy application zone 102). Energy application zone 102 may also include loss constituents that do not, themselves, absorb an appreciable amount of EM energy, but otherwise account for EM energy losses. Such loss constitutes may include, for example, cracks, seams, joints, doors, or any other loss mechanisms associated with energy application zone 102.

Energy application zones 102 may be part of a host apparatus or system, for example: an oven (e.g., a cooking oven, vending machine in which objects are processed once purchased), chamber, tank, dryer, thawer, dehydrator, reactor, engine, chemical or biological processing apparatus, furnace, incinerator, material shaping or forming apparatus, conveyor, combustion zone, cooler, freezer, filter etc.

In some embodiments, EM feedback related values may be received from the energy application zone. As used herein, EM feedback related values may include any received signal or any value calculated based on a receive signal(s), which may be indicative of the dielectric response of the cavity and/or the object to the applied RF energy. EM feedback related values may be MSE-dependent (i.e., each value may be associated with a respective MSE), for example, may include signals, the values of which may vary over different MSEs. EM feedback related values may include, for example, input and output power levels, network parameters—e.g., scattering parameters (S-parameters) and values derivable from the S-parameters and/or from the power levels, for example, input impedance (Zin), Dissipation ratio (DR), time or MSE derivative of any of them, Gamma ($\Gamma$) or any other value that may be derivable from the received signals.

An MSE as used herein may refer to a single combination of all the controllable RF energy application parameters that may be controlled in a given apparatus. For example, if only frequency in which RF energy is applied may be controlled in a given apparatus, each MSE may be a single frequency. If the apparatus includes more than one radiating element (e.g., antenna) and the phase between the two elements may be controlled in addition to the frequency, each MSE may include two parameters the frequency and the phase in which RF energy is applied. The concept of MSEs is broadly discussed below.

A change may be identified in at least some of the EM feedback related values in a period of time. A first set of EM feedback related values each associated with a particular MSE may be received from the energy application zone, at a first time. Optionally, a first amount of RF energy may be applied at two or more of the MSEs based on the received EM feedback related values. A period of time later, a second set of EM feedback related values may be received at the two or more MSEs, at a second time, and a change between the first and the second sets may be identified. For example, the time derivative of EM feedback related values associated with particular MSEs may be identified. The change may be identified by comparing an EM related value associated with a particular MSE received in the first set with EM related value associated with the same MSE received in the second set. Based on the identified change, a second amount of RF energy may be determined and applied to the energy application zone at two or more of the MSEs. Optionally the first and second feedback related values may be received at a single MSE, and the change in time between the two values may be determined, e.g., the time derivative of the EM feedback value at that MSE may be determined. The determined time derivative may be compared with a threshold value, and RF energy may be applied to the energy application zone at the single MSE if the time derivative is higher (or lower) than the threshold. In some embodiments, the time derivative value may be compared with two or more threshold values.

Apparatus 100 may include at least one radiating element 110 configured to apply RF energy to energy application zone 102. Radiating element 110 may be any element, system, array of elements, etc. designed or configured to transmit or deliver RF energy. For example, radiating element 110 may be any: antenna, an array of antennas, an RF feed, a waveguide, a slow wave antenna, a patch antenna etc. In the presently disclosed embodiments, more than one antenna and/or a plurality of radiating elements (e.g., antennas) may be provided. For example, radiating element 110 and 111 illustrated in FIG. 1A or radiating elements 110, 120 and 130 illustrated in FIG. 1B. The radiating elements may be located on one or more of surfaces (e.g., walls) that define zone 102. For example, as illustrated in FIG. 1B, elements 110 and 130 are located on two different walls of energy application zone 102. In some embodiments, the radiating element may be located inside zone 102 (e.g., element 130)

or at least partially located in zone 102 (e.g., elements 110 and 111). Additionally or alternatively, the radiating element may be located outside the energy application zone (e.g., element 120). One or more of the radiating elements (e.g., element 130) may be near to, in contact with, in the vicinity of or even embedded in object 103 (e.g., when the object is a liquid, or a filter). The orientation and/or configuration of each radiating element may be distinct or the same, based on the specific energy application, e.g., based on a desired target effect. Furthermore, the location, orientation, and configuration of each radiating element may be predetermined before applying energy to the object or may be dynamically adjusted during operation of the apparatus and/or between rounds of energy application. The invention is not limited to radiating elements having particular structures or locations within the apparatus.

As represented by the diagram of FIG. 1A, apparatus 100 may include at least one radiating element (e.g., 110 or 111) for emitting EM energy to energy application zone 102. At least one radiating element (e.g., 111 or 110) may also be configured to receive EM energy from energy application zone 102. In other words, radiating element, as used herein may function as an emitter, a receiver, or both, depending on a particular application and configuration. When a radiating element acts as a receiver of EM energy from an energy application zone (e.g., reflected and/or coupled EM waves), the radiating element receives EM energy from the energy application zone.

Some aspects of the present invention may involve detecting, measuring or sensing of the RF energy emitted from the radiating element to the energy application zone or received at the radiating element from the energy application zone. A detector configured to measure and/or detect various parameters of the emitted and/or received RF energy may be associated with at least one radiating element. The detector may detect and/or measure EM feedback related to the RF energy emitted and/or received. The EM feedback may include all detectable parameters of the RF energy, for example: power, frequency, energy, current, voltage, phases between emissions etc. For example, detector 118, illustrated in FIG. 1A, may be associated with elements 110 and 111. Detector 118 may be configured to measure or detect the parameters of the RF energy emitted from element 110 to zone 102 and the RF energy received from zone 102 to element 111, for example as a result of the RF energy emission from element 110. In some embodiments, detector 118 may be configured to detect also the parameters of the RF energy received from zone 102 (i.e., reflected back) at element 110 as result of the RF energy emission from element 110. Detector 118 may also include suitable types of circuits or devices that measure the voltage and current at the ports of radiating elements 110 and 111. In some embodiments, detector (e.g., detector 118 118a, 128 and 138) may include a directional coupler, configured to allow signals to flow from the RF source (e.g., source 112) to the radiating elements when the radiating elements function as emitters, and to allow signals to flow from the radiating elements to the detector when the radiating elements function as receivers.

In some embodiments, a single detector 118 may be associated with two radiating elements (e.g., elements 110 and 111). In some embodiments, each element may be associated with a respective detector, for example elements 110, 120 and 130 may be associated with detectors 118a, 128 and 138 illustrated in FIG. 1B. Detectors 118a, 128 and 138 may be configured to detect RF energy parameters of both the emitted and the received RF energy from zone 102. For example, RF energy may be emitted from element 110 to zone 102. As a result, a portion of the RF energy may be absorbed by or dissipated in object 103 and another portion may be reflected back and received by elements 110, 120 and 130.

Consistent with the presently disclosed embodiments, energy may be supplied to one or more emitting radiating elements, from RF source. Energy supplied to the emitting element may be referred to herein as supplied energy, and denoted as S.

Some of the supplied energy may be absorbed by the object (e.g., object 103) this energy may be referred to herein as absorbed energy or dissipated energy, and denoted as A.

A portion of the supplied RF energy may be reflected back to the emitting element, and may be referred to herein as reflected energy, denoted as R. The reflected energy may be reflected at the interface between the element and the energy application zone, and/or may be reflected from the energy application zone.

The rest of the emitted energy may be coupled to other elements (for example, the receiving radiating elements, another emitting radiating element 120 and 130, a sensor, e.g., sensor 140. Etc.), and may referred to herein as coupled energy denoted as C.

In some embodiments, all the supplied RF energy may be either reflected back to the emitting radiating element, or absorbed in the object, or coupled to another element, according to Equation (1):

$$S = R + A + C \qquad (1)$$

The difference between the amount of energy supplied to a radiating element and the amount of energy reflected back to that radiating element may be referred to herein as delivered energy (D). One or more detectors (e.g., detectors, 118, 118a, 128 and 138) may be configured to detect and measure the supplied energy (S), reflected energy (R), delivered energy (D) or coupled energies (C), and a controller (e.g., controller 150) may determine the delivered and/or absorbed amounts of energy, for example, based on equation (1). This may result in the following equations:

$$A = S - (R + C) \qquad (2a)$$

$$D = S - R \qquad (2b)$$

$$D = A + C \qquad (2c)$$

In accordance with some embodiments of the invention, an apparatus or method may involve the use of at least one source configured to supply EM energy to the energy application zone. For example, source 112 may supply RF energy to radiating element 110, source 122 may supply RF energy to radiating element 120 and source 132 may supply RF energy to radiating element 130. A source (also referred as a source of EM energy) may include any component(s) that is suitable for generating and supplying EM energy. Source 112 may include one or more of a power supply 113 and sources 122 and 132 may include one or more of power suppliers 123 and 133 configured to generate EM waves that carry EM energy. For example, power supply 113 (or 123 or 133) may be a magnetron configured to generate high power microwave waves at a predetermined wavelength or frequency. Alternatively, or additionally, power supply 113 (or 123 or 133) may include a semiconductor oscillator, e.g., a voltage controlled oscillator, configured to generate AC waveforms (e.g., AC voltage or current) with controllable frequency. The frequency may be controlled to be constant or to vary. AC waveforms may include sinusoidal waves, square waves, pulsed waves, triangular waves, or another type of waveforms with alternating polarities. Alternatively, or additionally, a source of EM energy may include any other power supply, e.g., EM field generator, EM flux generator, solid state amplifier or any mechanism for generating vibrating electrons.

Consistent with some embodiments of the invention, RF energy may be supplied to the energy application zone in the form of propagating EM waves at predetermined wavelengths or frequencies (also known as electromagnetic radiation). As used consistently herein, propagating EM waves may include resonating waves, traveling waves, evanescent waves, and waves that travel through a medium in any other manner. EM radiation carries energy that may be imparted to (or dissipated into) matter with which it interacts.

In some embodiments, the source (e.g., source 112, 122 or 132) may further include at least one modulator (e.g., modulator 115, 125 or 135) and/or at least one amplifier (e.g., amplifier 116, 126 or 136). The amplifier may be any apparatus configured to change the amplitude of the RF waves supplied by the power supply. It is to be noted that the source (e.g., source 112, 122 or 132) may include only one component or more than one component or any combination of components according to the demand of the invention particular embodiment. The power supply, the modulator and the amplifier may each be controlled by one or more controllers (e.g., controller 150), which is discussed below.

Apparatus 100 may further include at least one sensor. Sensor 140 may be installed in or around energy application zone 102. Sensor 140 may be configured to detect and/or measure an EM feedback, in accordance with some embodiments of the invention, for example the intensity of EM field excited in the energy application zone. Additionally or alternatively, sensor 140 may be configured to detect and/or measure other signals or feedbacks related to a property the object (e.g., processing state) or the energy application zone. For example, sensor 140 may be any thermometer configured to measure the temperature of the object and/or the energy application zone (e.g., a thermocouple or an IR sensor). Sensor 140 may be a humidity sensor, a pressure sensor (e.g., a barometer), a pH sensor configured to measure the pH of a solution when the object comprises liquids. Sensor 140 may be configured to measure the weight of at least a portion of the object (e.g., a scale). The sensor may be configured to send feedback signals to controller 150.

In some embodiments, apparatus 100 may include a controller (150). As used herein, the term controller is interchangeable with the term processor and may include any electric circuit that performs a logic operation on input or inputs. Controller 150 may be any computer or processor configured to execute instructions included in a software program, for example execute the methods disclosed herein. For example, such a controller may include one or more integrated circuits, microchips, microcontrollers, microprocessors, all or part of a central processing unit (CPU), graphics processing unit (GPU), digital signal processors (DSP), field-programmable gate array (FPGA) or other circuit suitable for executing instructions or performing logic operations.

The instructions executed by the controller may, for example, be pre-loaded into a memory included in the processor or may be stored in a separate memory unit, such as a RAM, a ROM, a hard disk, an optical disk, a magnetic medium, a flash memory, other permanent, fixed, or volatile memory, or any other mechanism capable of storing instructions for the controller. The separate memory unit may or may not be a part of the controller. The controller(s) may be customized for a particular use, or can be configured for general-purpose use and can perform different functions by executing different software.

If more than one controller or processor is employed, all may be of similar construction, or they may be of differing constructions electrically connected or disconnected from each other. They may be separate circuits or integrated in a single circuit. When more than one controller or processor is used, they may be configured to operate independently or collaboratively. They may be coupled electrically, magnetically, optically, acoustically, mechanically or by other means permitting them to interact.

In some embodiments, at least one controller may be configured to cause RF energy application via at least one radiating element to the energy application zone. As used herein, if a machine (e.g., a controller) is described as configured to perform a task (e.g., configured to cause application of a predetermined field pattern), then, in some embodiments, the machine performs this task during operation. Similarly, when a task is described as being done in order to establish a target result (e.g., in order to apply a plurality of EM field patterns to the object), then, in some embodiments, carrying out the task may accomplish the target result. As used herein, the term predetermined means only that the associated quantity or value is calculated or otherwise determined before processing is completed. Predetermined values may include values stored in memory; values calculated, observed, measured, read into, received, etc. before commencement of EM energy processing; or any values calculated, observed, measured, read into, received, etc. during such processing.

Controller 150 may control at least one RF source (e.g., sources 112, 122 or 132) to supply RF energy to at least one radiating element (e.g., elements 110, 120 and 130), to cause the radiating elements to emit the RF energy to energy application zone 102. The controller may control the source to supply RF energy to the radiating element at specifically chosen MSEs or a set of MSEs. RF energy at the set of MSEs may be supplied sequentially or simultaneously.

The term modulation space (MS) is used to collectively refer to all the parameters that may affect a field pattern in the energy application zone and all combinations thereof. In some embodiments, the MS may include all possible components that may be used for applying RF energy to the zone and their potential settings (absolute and/or relative to others) and adjustable parameters associated with the components. For example, the MS may include a plurality of variable parameters, the number of antennas, their positioning and/or orientation (if modifiable), the useable bandwidth, a set of all useable frequencies and any combinations thereof, power settings, phases, amplitudes, the number of other adjustable components located in the energy application zone (e.g. magnetizable elements or conductive elements) and their controlling parameters (e.g. the amount of the magnetic field or the state of the conductive element) and to some extent-polarization, etc. The MS may have any number of possible variable parameters, ranging between one parameter only (e.g., a one-dimensional MS limited to frequency only or phase only-or another single parameter), two or more dimensions (e.g., varying frequency and amplitude or varying frequency and phase together within the same MS), or many more.

Each variable parameter associated with the MS is referred to as an MS dimension. For example, a three dimensional modulation space may include three dimensions designated as frequency (F), phase (P), and amplitude (A). That is, frequency, phase, and amplitude (e.g., an amplitude difference between two or more waves being transmitted at the same time) of the EM waves are modulated during energy application, while all the other parameters may be fixed during energy application. In one example, a one-dimensional modulation space oven may provide MSEs that differ one from the other only by frequency.

As noted, a Modulation Space Element (MSE) may refer to a specific set of values of the variable parameters in MS. Therefore, the MS may also be considered to be a collection of all possible MSEs. For example, two MSEs may differ one from another in the relative amplitudes of the energy being supplied to a plurality of radiating elements. For example, a three-dimensional MSE may have a specific frequency, F(i), a specific phase, P(i), and a specific amplitude, Am(i). If even one value of these MSE variables changes, then the new set defines another MSE. For example, (3 GHz, 30°, 12 V) and (3 GHz, 60°, 12 V) are two different MSEs, although only the phase component is different.

Differing combinations of these MS parameters will lead to differing field patterns across the energy application zone and differing energy distribution patterns in the object. A plurality of MSEs that can be executed sequentially or simultaneously to excite a particular field pattern in the energy application zone and the amounts of RF energy applied at each MSE may be collectively referred to as an energy application protocol. For example, an energy application may consist of three MSEs: (F(1), P(1), Am(1)); (F(2), P(2), Am(2)) (F(3), P(3), Am(3)) and three RF energy amounts S(1), S(2) and S(3). Such an energy application protocol may result in applying the first, second, and third MSE to the energy application zone at the respective amounts.

The invention is not limited to any particular number of MSEs or MSE combinations. Various MSE combinations may be used depending on the requirements of a particular application and/or on a desired energy application profile, and/or given equipment, e.g., cavity dimensions. The number of options that may be employed could be as few as two or as many as the designer desires, depending on factors such as intended use, level of desired control, hardware or software resolution and cost.

In some embodiments, the controller may control the RF energy by choosing a sub-group (also referred as sub-set) of MSEs from a plurality of available MSEs. The available MSEs may include all the possible combinations of different components and parameters in a particular RF energy application apparatus (i.e. the MS of a particular apparatus). An energy application protocol 100 may include selecting a particular frequency, phase and amplitude at which to apply RF energy via one or more radiating elements. The energy application protocol may further include assigning different or similar energy levels to the selected MSEs, for example by varying respective durations in which a particular EM field is excited in the energy application zone, e.g., energy at a particular MSE is applied. The selection of the sub-group of MSEs and/or the corresponding energy level at each MSE may be determined based on a feedback, e.g., an EM feedback, received from the energy application zone.

In certain embodiments, the at least one controller may be configured to determine an EM feedback-related values such as a value indicative of EM energy absorbable by the object at each of a plurality of MSEs. The determination may be done based on an EM feedback received from the energy application zone during energy application at a particular MSE. The value determined for each MSE may be used to select the sub-group of MSEs in which EM energy is to be applied at a particular energy application protocol. For example, controller 150 may select to cause RF energy application at all MSEs associated with EM feedback-related values (e.g., value indicative of EM energy absorbable by the object) higher or lower than a threshold. In some embodiments, other EM feedback-related values may be used to select the sub-group of MSEs, and additional rules (not just setting a threshold for values) may be applied. While the invention is not limited to any particular measure of EM feedback-related values, various exemplary indicative values (EM feedback-related values) are discussed below.

In order to associate an EM feedback value with a particular MSE, a sweep may be conducted. As used herein, a sweep may include, for example, the application over time of energy at more than one MSE. For example, a sweep may include the sequential transmission of energy at multiple MSEs in one or more contiguous MSE bands; the sequential transmission of energy at multiple MSEs in more than one non-contiguous MSE bands; the sequential transmission of energy at individual non-contiguous MSEs; and/or the transmission of synthesized pulses having a desired MSE/power spectral content (e.g., a synthesized pulse in time). The MSE bands may be contiguous or non-contiguous. Thus, during an MSE sweeping process, the at least one controller may regulate the energy supplied from a source (e.g., source 112) to the at least one radiating element to sequentially apply EM energy at various MSEs to zone 102, and to receive EM feedback values from zone 102 associated with each MSE. The EM feedback-related values may serve as indicators (values indicative) of the EM energy absorbable by object 103 at each MSE.

During the sweeping process, controller 150 may be regulated to receive an EM feedback-related values indicative of the EM energy reflected and/or coupled at radiating elements (for example elements 110, 120 and 130), for example S-parameters. Controller 150 may then determine an EM feedback-related value (e.g., a value indicative of EM energy absorbable by object 103) at each of a plurality of MSEs based on the received information, for example, DR. Consistent with some of the presently disclosed embodiments, a value indicative of the absorbable energy may include a dissipation ratio (DR) associated with each of a plurality of MSEs. As referred to herein, a DR (or absorption efficiency or power efficiency), may be defined as a ratio between EM energy absorbed by object 103 and EM energy supplied into EM energy application zone 102. In some embodiments, a DR may be defined as a ratio between EM energy absorbed by object 103 and EM energy delivered into EM energy application zone 102.

In some of the presently disclosed embodiments, a DR may be calculated using equation (1):

$$DR = A/S \qquad (1)$$

wherein S is the energy supplied to a emitting radiating element and A is the energy absorbed in the object. Both S and A may be calculated by integrating, over time, power detected by power detectors (e.g., detectors 118, 118a, 128 or 138). For t=ti, wherein ti may be any moment in time during which energy is applied to the energy application zone, equation (1) may have the form:

$$DR = P_A/P_S; \qquad (1^*)$$

Wherein $P_A$ is the power absorbed and $P_S$ the power supplied. $P_A$ may be evaluated using equation (2):

$$P_A = P_S - P_{out}; \qquad (2)$$

wherein $P_{out}$ stands for the power detected by all the detectors (e.g., radiating elements), denoted as $P_{detect}(i)$ in the $i^{th}$ detector, in and around the energy application zone, when $P_S$ was supplied (applied) by a radiating element at a certain MSE, see equation (3):

$$P_{out} = \Sigma P_{detect}(i) \tag{3}$$

If the only available detectors are the one associated with the radiating elements, DR may be calculated using three detected power parameters $P_S$, $P_R$ and $P_C$ and equation (1*) may have the form of equation (4):

$$DR = (P_S - P_R - P_C)/P_S \tag{4}$$

where $P_S$ represents the EM energy and/or power supplied to emitting radiating element 110, $P_R$ represents the EM energy and/or power reflected/returned to the emitting radiating element, and $P_C$ represents the EM energy coupled to the other radiating elements (e.g., 120 and 130) function as receiving elements. DR may be a value between 0 and 1, and thus may be represented by a percentage number.

For example, consistent with an embodiment which is designed for three radiating elements 110, 120, and 130, controller 150 may be configured to determine the input reflection coefficients $S_{11}$, $S_{22}$, and $S_{33}$ and transfer coefficients $S_{12}$, $S_{21}$, $S_{13}$, $S_{31}$, $S_{23}$, and $S_{32}$ (also known as S-parameters) based on measured power and/or energy information during the sweep. Accordingly, the DR corresponding to radiating element 1 may be calculated based on the above mentioned reflection and transmission coefficients, according to equation (5):

$$DR_1 = 1 - (|S_{11}|^2 + |S_{12}|^2 + |S_{13}|^2). \tag{5}$$

As shown in equation (5), the DR may be different at different radiating elements. Thus, in some embodiments, amount of energy supplied to a particular radiating element may be determined based on the DR associated with that particular radiating element.

When plotting each of the DR (MSE) versus time [DR(t)(MSE)], some of the plotted curves may show variation in the value of DR over time (e.g., the time derivative of DR(MSEi) may be higher than a threshold). In some embodiments, changes in time in the DR(MSEi) may indicate whether energy applied to the energy application zone at that particular MSEi may be mostly dissipated in the object, or may be dissipated elsewhere in the energy application zone (e.g., in accessories in the zone-such as: tray). An MSEi associated with DR(t) that exhibits changes in a period of time higher than a threshold (i.e., the time derivative is higher than a first threshold) may indicate that RF energy applied at that MSE may be mostly dissipated in the object. In some embodiments, dielectric properties of an object processed by RF energy may change during the RF energy application. For example, dielectric properties of food items may change as cooking proceeds, e.g., due to changes in physical properties of the food items, such as temperature and water content. On the other hand, other components located in the energy application zone may not demonstrate significant (or any) changes in their dielectric properties due to RF energy application. Dielectric properties of components such as the cavity, door, joints, trays, shelves, etc. may have minor (if any) change due to the RF energy application. In some embodiments, fast change or non-continuous change in DR(MSEi) (e.g., time derivative is higher than a second threshold higher than the first threshold) may be associated with changes in the zone (e.g., changes in accessories in the zone- for example: metal melting, arcing).

An EM feedback, for example, DR, may indicate how much of the energy supplied to the energy application zone is dissipated (or absorbed), either in the object or in other components in the energy application zone. In some embodiments, an efficiency of the RF energy application may be increased by applying energy at MSE(s) that may dissipate more readily in the object, for example MSEs associated with a time derivative of the EM feedback (e.g., DR) higher than a threshold.

In certain embodiments, controller 150 may be configured to determine an RF energy application protocol by adjusting the amount of RF energy supplied at each MSE based on the EM feedback received from energy application zone 102 or calculated using a received EM feedback during sweeping over a plurality of MSEs. In some embodiments, an RF energy application protocol may be determined based on the identified changes in the DR(MSEi). In some embodiments, the change within a period of time may be identified between $[DR(MSEi)]^2$ received at $t_1$ and $t_2$ or any other values derivable from the DR(MSEi) or the S-parameters. Other methods for identifying changes or distance between two EM-feedback related values may be used- for example: changes may be identified by comparing DR(MSE) at $t=t_i$ to DR(MSE) at $t=t_i-1$, or $t=t_i-2$ or to DR(MSE) at $t=0$ ($t_0$). In other examples, changes may be identified by comparing DR(MSE) at $t=n^2$ to DR(MSE) at $t=(n-1)^2$. In some embodiments, smoothing functions may be used to decrease noise in order to calculate the changes or distance between two values.

In some embodiments, higher RF energy (e.g., more time and/or power) may be applied to an MSEi associated with a DR(t)(MSE) having higher time derivatives than to an MSEi associated with a DR(t)(MSE) having a lower time derivative (lower than a threshold). In some embodiments, zero RF energy may be applied at MSEs associated with DR(t)(MSE) derivative values lower than a predetermined threshold, as such MSEs may be associated with RF energy dissipation in components other than the object.

Additionally or alternatively, controller 150 may determine the RF energy application protocol based on the DR values. DR(MSEi) may be used to determine the amount of energy to be supplied at each MSEi as a function of the DR(MSEi). In some embodiments, the energy applied at MSEi may be inversely related to the DR(MSEi). Such an inverse relationship may be applied to other EM feedbacks and other values indicative of EM energy absorbable and may involve a general trend. For example, when the value indicative of absorbable energy in a particular MSE subset (i.e., one or more MSEs) tends to be relatively high, the actual supplied energy at that MSE subset may be relatively low. When an indicator of absorbable energy in a particular MSE subset tends to be relatively low, the supplied energy may be relatively high. This substantially inverse relationship may be even more closely correlated. For example, the supplied energy may be set such that its product with the absorbable energy value (i.e., the absorbable energy by object 103) is substantially constant across the MSEs applied. In other embodiments, other relations may be applied, for example a constant amount of energy may be applied at at least a sub-group of MSEs. Another EM feedback related value according to the invention may be the complex input impedance of a radiating element, denoted herein as Zin, its real part, denoted Real(Zin), or its imaginary part, denoted Img(Zin). The controller may associate each of the Real(Zin) and Img(Zin) values measured on each one of the radiating elements when RF energy was applied to the energy application zone at a particular MSE. The controller (e.g., controller 150) may further be configured to identify changes within a period of time (time derivatives of Real(Zin) and/or Img(Zin)) in the input impedance. The controller may determine RF energy application protocol based on the measured Real(Zin) and/or Img(Zin) and/or based on the respective time derivatives.

Some exemplary RF energy application protocols may have higher RF energy application efficiencies than other RF energy application protocols. An efficiency may refer to a ratio between the RF energy supplied to the energy application zone and the RF energy that dissipated in the object (e.g., A/S), and not in other components located in energy application zone 102 (e.g., elements associated with a cavity, such as door, tray(s), lines, joints, etc.). In some embodiments, an RF energy application having a high efficiency may be associated with high A/S ratio(s) or A/S ratios above a predetermined level. In some embodiments, efficient RF energy application may be associated with minimal or substantially minimal (e.g., zero or substantially zero) energy dissipated in other components, which are not the object to be processed, located in the energy application zone.

Controller 150 may adjust the energy application to the energy application zone depending on EM feedback. For example, for MSEs associated with a time differences (e.g., derivative) of the EM feedback higher than a certain threshold, controller 150 may cause application of EM energy at those MSEs at a level higher than at MSEs associated with time differences of the EM feedback lower than a certain threshold. For example, some of the RF energy applied may be better absorbed by the object at a first group of MSEs and some of the RF energy applied may be better absorbed by elements included in the energy application zone (e.g., cavity, trey, nuts, gasket, etc) at a second group of MSEs. This may be detected by identifying the changes in one or more of the EM feedback related values within a period of time (e.g., time differences). An object, when processed by application of RF energy, may change one or more of it's properties (e.g., a temperature, volume, etc.). This change may be continuous and may cause a continuous change in the dielectric properties of the object, thus may cause a continuous change(s) in the values derivable from (e.g., EM feedback related values). MSEs that are associated with a continuous change in the values derivable from may be included in the first group of MSEs. On the other hand, the energy application zone's (e.g., the cavity) dielectric properties are not expected to change during or following the RF energy application, thus small or even no change in the EM feedback-related values may be detected. MSEs associated with a small (e.g., lower than a first threshold) changes in the EM feedback-related values may be included in the second group of MSEs.

Additionally or alternatively, MSEs associated with a non-continuous (e.g., discrete change or a change higher than a second threshold, the second threshold is (much) higher than the first threshold) changes in the EM feedback-related values may be included in the second group of MSEs. A non-continuous change (e.g., discrete) may refer to a singular or abrupt change—e.g., when a sudden change in the EM feedback-related values is detected. Non-continuous changes may occur due to for example, sparks or arcing in the cavity (e.g., electric shortages) those changes, when identified and associated with an MSE may suggest that this MSE belongs to the second group.

An exemplary energy application protocol according to some embodiments of the invention may include identifying object related MSEs and applying RF energy at two or more of the object related MSEs (e.g., in an amount inversely related to EM feedback values (e.g., DR(MSEi)) associated with those MSEs). The processor may further determine other amounts of energy (e.g., zero) to be applied at two or more cavity related MSEs. Another exemplary energy application protocol may include identifying object related MSEs and applying RF energy at the object related MSEs in a predetermined (constant) amount. In some embodiments, for MSEs that differ one from the other only by frequency, those frequencies may be referred to as object related frequencies.

In some embodiments, controller 150 may be configured to hold substantially constant the amount of time at which energy is supplied to radiating elements (e.g., elements 110, 120 and 130) at each MSE, while varying the amount of power supplied at each MSE (e.g., as a function of the absorbable energy value). In some embodiments, controller 150 may be configured to cause the energy to be supplied to the radiating element at a particular MSE or MSEs at a power level substantially equal to a maximum power level of the device and/or the amplifier at the respective MSE(s) or other constant value.

Alternatively or additionally, controller 150 may be configured to vary the period of time during which energy is applied to each MSE (e.g., as a function of the absorbable energy value). At times, both the duration and power at which each MSE is applied are varied. Varying the power and/or duration of energy supplied at each MSE may be used to cause substantially uniform energy absorption in the object or to have a controlled spatial pattern of energy absorption, for example, based on EM feedback. Consistent with some embodiments, controller 150 may be configured to cause the RF source (e.g., by controlling the amplifier) to supply different amounts of energies at different MSEs, for example by supplying RF energy based on different relationships between the EM feedback at each MSE at various sub-groups (e.g., sets) of MSEs.

Because absorbable energy and other EM feedbacks can change based on a host of factors including object temperature, in some embodiments, it may be beneficial to regularly update the EM feedback values and adjust energy application based on the updated values. These updates can occur multiple times a second, or can occur every few seconds or longer, depending on the requirements of a particular application.

Controller 150 may be further configured to control the RF energy application by controlling various aspects of the RF energy source (e.g., sources 112, 122 and 132). In accordance with some embodiments, controller 150 may regulate modulations performed by the modulator (e.g., modulator 115, 125 and 135). In some embodiments, the modulator may include at least one of a phase modulator, a frequency modulator, and an amplitude modulator configured to modify the phase, frequency, and amplitude of an AC waveform generated by the power supply (e.g., power supply 113, 123 and 133) connected to the modulator.

In some embodiments, apparatus 100 may include a phase modulator (not illustrated) that may be controlled to perform a predetermined sequence of time delays on an AC waveform, such that the phase of the AC waveform is increased by a number of degrees (e.g., 10 degrees) for each of a series of time periods. In some embodiments, controller 150 may dynamically and/or adaptively regulate modulation based on feedback from the energy application zone. For example, controller 150 may be configured to receive an analog or digital EM feedback signal from detector 118 and may dynamically determine a time delay at the phase modulator for the next time period based on the received feedback signal.

In some embodiments, the source of EM energy may be configured to supply EM energy at a plurality of phases, and the controller may be configured to cause the transmission of energy at a subset of the plurality of phases. By way of example, the phase modulator may include a phase shifter. The phase shifter may be configured to cause a time delay in the AC waveform in a controllable manner within zone 102, delaying the phase of an AC waveform anywhere from between 0-360 degrees. In some embodiments, phase difference between two signals supplied to radiating elements may be obtained directly from the power source—for example: the output frequency and the phase emitted from each radiating element may be determined by the source (for example: by using Direct Digital Synthesizer).

In some embodiments, apparatus 100 may include a frequency modulator (not illustrated). The frequency modulator may include a semiconductor oscillator configured to generate an AC waveform oscillating at a predetermined frequency. The predetermined frequency may be in association with an input voltage, current, and/or other signal (e.g., analog or digital signals). For example, a voltage controlled oscillator may be configured to generate waveforms at frequencies proportional to the input voltage.

Controller 150 may be configured to regulate an oscillator (not illustrated) to sequentially generate AC waveforms oscillating at various frequencies within one or more predetermined frequency bands. In some embodiments, a predetermined frequency band may include a working frequency band, and the processor may be configured to cause the application of energy at frequencies within a sub-band of the working frequency band. A working frequency band may include a collection of frequencies selected because, in the aggregate, they achieve a desired goal, and there is diminished need to use other frequencies in the band if that sub-portion achieves the goal. Once a working frequency band (or subset or sub-portion or a sub group or sub-band thereof) is identified, the controller may sequentially apply power at each frequency in the working frequency band. This sequential process may be referred to as frequency sweeping. In some embodiments, based on the feedback signal provided by detector 118 or based on changes identified in EM-feedback related value, controller 150 may be configured to select one or more frequencies or sub-bands from a frequency band, and regulate an oscillator to sequentially generate AC waveforms at these selected frequencies.

Alternatively or additionally, controller 150 may be further configured to regulate amplifier 116 (or amplifiers 126 and 136), to adjust amounts of energy delivered via radiating element 110, based on the feedback signal.

In some embodiments, the apparatus may include more than one source of RF energy, as illustrated in FIG. 1B. For example, more than one oscillator may be used for generating AC waveforms of differing frequencies. The separately generated AC waveforms may be amplified by one or more amplifiers. Accordingly, at any given time, the radiating elements may be caused to simultaneously emit EM waves at, for example, two differing frequencies to zone 102. Alternatively, the radiating elements may be caused to simultaneously emit EM waves at a common frequency with a phase difference between the radiating elements.

The controller may be configured to regulate an amplitude modulator in order to alter amplitude of at least one EM wave supplied to the energy application zone. In some embodiments, the source of EM energy may be configured to supply EM energy in a plurality of amplitudes, and the controller may be configured to cause the transmission of energy at a subset of the plurality of amplitudes. In some embodiments, the apparatus may be configured to supply EM energy through a plurality of radiating elements, and the controller may be configured to supply energy with differing amplitudes simultaneously to at least two radiating elements.

In some embodiments, apparatus 100 may include interface 160. Controller 150 may be configured to receive from interface 160 one or more processing instructions and/or other information related to the object or the processing of the object. Interface 160 may be any user interface, e.g., a graphical user interface (GUI), a touch screen, a keypad, a screen associated with a mouse etc. Additionally or alternatively, interface 160 may include a device capable of reading and receiving information from a machine readable element (for example: a barcode or an RFID tag), for example a barcode reader, an RFID reader etc. Additionally or alternatively, interface 160 may be connected to a host apparatus (e.g., oven). Controller 150 may be configured to determine the energy application protocol solely based on the information received from interface 160 or in combination with the EM feedback received or calculated form a signal detected by at least one detector (e.g., detectors 118, 128 and 128) and/or at least one sensor (e.g., sensor 140).

Some aspects of the invention may be related to application of RF energy to an energy application zone located at least partially inside a cavity. EM energy application zone may be part of a cavity or may consist the interior of a cavity A cavity may be any void comprising at least one wall made from a material substantially opaque to RF energy. Optionally more than one wall or all cavity walls are made from materials opaque to RF energy. For example, an oven constructed from cast iron, stainless steel, or aluminum alloys or other metals and alloys suitable for constructing a cavity. Alternatively, the at least one wall may comprise a dielectric material at least partially transparent to RF energy and coated by a coating made from material substantially opaque to RF energy. A material substantially opaque to RF energy may include any material capable of blocking or reflecting RF energy above a predetermined threshold (e.g., above 90%). Some exemplary cavities in accordance the embodiments of the invention are illustrated in FIG. 2.

FIG. 2 presents a diagrammatic representation of a cavity 200 in accordance with some embodiments of the invention. Cavity 200 may include cavity body 202. Cavity body may be configured to hold at least a portion of an object (e.g., object 103). Cavity body 202 may comprise at least one wall constructed from or coated by, a material substantially opaque to RF energy. Cavity body 202 may have a rectangular shape (as illustrated), cylindrical shape, or may have any other shape according to demand of the use of the cavity. Cavity 200 may further comprise at least one radiating element 204. Radiating elements 204a, 204b and 204c may be any elements configured to emit and/or receive RF energy from the cavity according to the invention. The radiating elements may be connected to an RF source and to a controller (e.g., controller 150). In some embodiments, one or more radiating elements (e.g., element 204a) may be installed in proximity to at least one cavity wall. In some embodiments, one or more radiating elements (e.g., 204b) may be installed outside the cavity, in proximity to a cavity wall optionally having an RF transparent window 205. The RF transparent window may be constructed from any dielectric material capable of transferring at least a portion of the RF energy emitted from element 204b. In some embodiments, the RF transparent window may cover the entire wall. In some embodiments, one or more radiating elements (e.g., element 204c) may be located at least partially inside or placed in proximity to object 103. For example, element 204c may be immersed in a solution in a chemical reactor. In some embodiments, cavity 200 may include at least one sensor. Sensor 206 may be embedded in, immersed in or placed in proximity to object 103. Sensor 206 may be any sensor configured to measure a property of object 103. The property may include any measurable property, such as temperature, pressure, volume, pH, humidity ratio, density, moisture, etc. Additionally or alternatively, the property may include other characteristics, such as color, taste, doneness, smell, etc. In some embodiments, one or more properties may be monitored (e.g., detected) by sensor 206. In some embodiments, sensor 206 may be configured to measure EM feedback from cavity 200. For example, sensor 206 may be configured to measure the intensity of the EM field excited in cavity 200 (by the radiating elements) in the surroundings of object 103. Additionally or alternatively, sensor 208 may be installed in proximity or on at least one wall in cavity 200. Sensor 208 may be any sensor configured to measure a property of object 103 or cavity 200. Similarly to sensor 206, sensor 208 may sense one or more property of object 103 and/or of the surrounding of the object. In some embodiments, sensors 206 and 208 may sense the same properties. In some embodiments, sensors 206 and 208 may sense different properties, for example, sensor 206 may sense the temperature of the object and sensor 208 may sense humidity in cavity 200, outside object 103.

Figure 3:
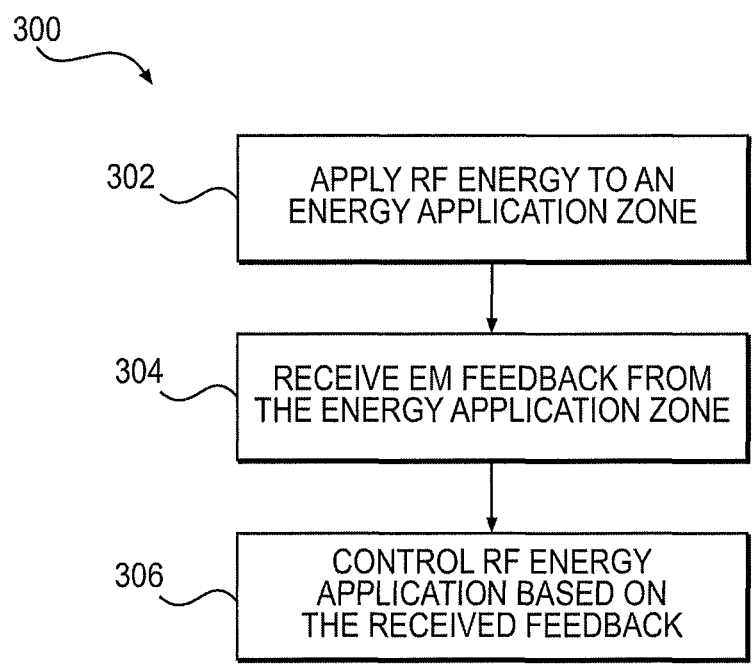
FIG. 3 is a flowchart of a method for applying EM energy to an energy application zone in accordance with some embodiments of the invention.

Method 300 for applying RF energy to an energy application zone in accordance with some embodiments of the invention is presented in the flowchart in FIG. 3. Method 300 described in method 300 may be executed by controller 150 and may be used for processing an object. In some embodiments, operations 302 and 304 may be used for detecting a processing state of an object and/or a change in the processing state of the object. The RF energy may be applied to the energy application zone (e.g., zone 102), in operation 302, via one or more radiating elements. In some embodiments, low amounts of RF energy may initially be applied at one or more MSEs. Low amounts of RF energy may be defined as amounts of RF energy applied to the energy application zone that result in little or no processing of the object (e.g., object 103) placed in the zone. For example, the low amounts of energy may not be sufficient to: cook a food item, thaw frozen object, cause or accelerate chemical reaction, etc. Low amounts of energy may be applied by for example, by applying low RF power from the RF source (e.g., source 112) or by applying high power for short periods of time. Alternatively, RF energy application in operation 302 may be conducted in energy levels sufficient to process an object placed in the energy application zone. The RF energy application in operation 302 may be conducted by sweeping over a plurality of MSEs (e.g., at a plurality of frequencies, phases and/or amplitudes), for example, by transmission over time of energy at more than one MSE. A controller (e.g., controller 150) may control the RF energy application by sweeping over a plurality of MSEs and assigning a constant (e.g., low) amount of energy to be applied at each MSE.

The controller may then receive EM feedback-related values from the energy application zone, in operation 304. EM feedback-related values may be detected at one or more radiating elements (e.g., element 110, 11, or 120) or at one or more sensors (e.g., sensor 140 or 206). EM feedback related values may include or may be calculate or derivable based on one or more network parameters, for example, one or more S-parameters, T-parameters, ABCD parameters, or the like. The network parameters may be of a system comprising the energy application zone which may include the object, e.g., a resonant cavity. In some embodiments, network parameters may have a magnitude and a phase, and may be represented by a complex number. In some embodiments, only the magnitude of the network parameter may be used as EM feedback-related values or as values indicative of energy absorbable in the object (or for calculations thereof). In some embodiments, phase values, by their own or in conjunction with the magnitude values of the network parameters may be used as (or for calculating) EM feedback—related values. EM feedback related values may be calculated or derivable based on one or more network parameters and additional parameters or inputs (e.g., the applied power at an MSE). In some embodiments, receiving EM feedback-related values may include detecting or sensing an EM signal or other feedback (e.g., detecting network parameters and/or other parameters that relate to energy application—e.g., power applied) and calculating or evaluating or deriving EM feedback-related values from this detection.

Each of the EM feedback-related values may be received as a result of the RF energy applied in operation 302. The EM feedback-related values may be associated with a respective MSE, from the plurality of MSEs swept in operation 302. The EM feedback-related values may be received from one or more sensors and/or detectors configured to measure EM feedback-related values in the energy application zone. The EM feedback-related values may include one or more of the following signals: the energy supplied to each emitting radiating element from the RF source, the energy reflected back from the zone at the emitting radiating elements, the energy coupled to the other radiating elements acting as receiving elements (when more than one radiating element is installed in the energy application zone), the input impedance measured on each radiating element, the S-parameters associated with each radiating element, etc. The EM feedback-related values may also include any mathematical manipulation of (e.g., values derivable from) the signals received from the energy application zone, for example, the DR, a time derivative of any of the signals, etc. In some embodiments the controller may be configured to identify a change in time of at least one of the received feedback-related values associated with a respective MSE, for example the controller may be configured to determine the time derivative of the DR(MSEi) (or $DR^2$ (MSEi)) and follow changes in the time derivative.

In operation 306, the controller may control or adjust RF energy application based on the received feedback-related values. In some embodiments, the controller may control or adjust RF energy application based on identified change in one or more of the EM feedback-related values within a period of time. For example, the controller may select to apply RF energy at MSEs associated with EM feedback-related values (e.g., a time derivative of the DR(MSEi)) lower or higher than a threshold. Additionally or alternatively, the controller may adjust the RF energy amounts applied at each MSE as a function of the EM feedback-related value at that MSE. In some exemplary embodiments, the controller may cause application of RF energy at each MSE in an amount inversely related to the DR value at that MSE. In some embodiments, the controller may select a sub-set of MSEs (e.g., sub-band of frequencies) based on an identified change in the EM feedback related values within a period of time. In some embodiments, the controller may not apply RF energy or may apply a low amount of energy at MSEs that may cause the RF energy to be dissipated in the elements included in the energy application zone (refers herein as cavity related MSEs). In some embodiments, the controller may only apply RF energy at MSEs that may cause the RF energy to be dissipated in the object (refers herein as object related MSEs)-for example: a predetermined (constant) amount of energy may be applied at object related MSEs or an amount of energy inversely related to the DR values may be applied at object related MSEs.

In some embodiments, an energy application protocol may be set based on EM feedback-related values received from the energy application zone. For example, the energy application protocol may be set based on the DR, a mean DR and Zin. Alternatively, the energy application protocol may be set based on a time derivative of the DR and/or the DR. The energy application protocol may further include a decision not to apply RF energy at MSEs that are not related to the object and to apply RF energy at object related MSEs. In some embodiments, the object related MSEs may be identified by monitoring the time derivative of the DR or any other value indicative of energy absorbed by the object. An energy application protocol may include one or more rules at which RF energy may be applied to the energy application zone. The rules may control the selection of the MSEs from the plurality of MSEs to which RF energy may be applied. For example, the rule may include applying RF energy at MSEs associated with a continuous change in EM feedback-related values. Additionally or alternatively, the rules may determine the amount of energy to be applied at each MSE, for example by setting a weigh for each MSE -e.g.,amounts of power and/or time supplied to each radiating element (e.g., element 110, 120 and 130) from the RF energy source (e.g., source 112, 122 and 132).

RF energy may be applied to the energy application zone according to the energy application protocol set. In some embodiments, controller may cause application of RF energy-e.g., by controlling RF source or other components in apparatus 100. The RF energy may be applied via one or more radiating elements connected to one or more RF sources. The RF source may be controlled by the controller to supply the RF energy to the radiating element(s) according to the protocol set. In some embodiments, e.g., for detecting a processing state of an object and/or a change in the processing state of the object, operation 306 may be replaced by operation 760 described in method 700.

Figure 4A:
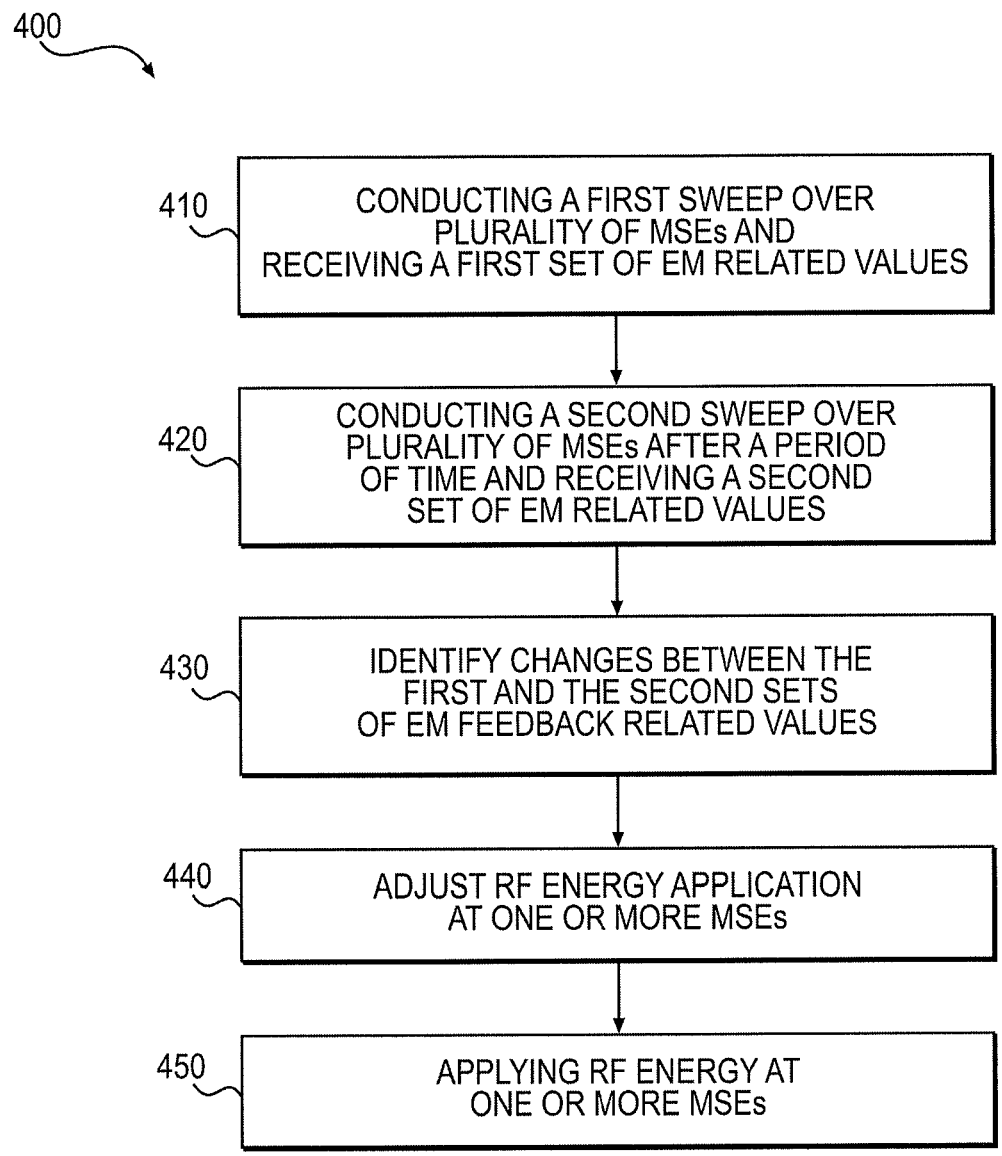
FIG. 4A is a flowchart of a method for adjusting RF energy application according to changes identified within a period of time in EM feedback related values, according to some embodiments of the invention.

FIG. 4A shows a method 400 for applying EM energy according to changes identified within a period of time in EM feedback-related values, in accordance with some embodiments of the invention. A first sweep over a plurality of MSEs may be conducted, and a first set of EM feedback related values may be received, in operation 410. A controller may associate each of the MSEs with an EM feedback-related value within the first set. The first sweep may be conducted similarly to the sweep disclosed in operation 302 included in method 300. After a period of time (for example, every 60 seconds as disclosed in respect to the graph shown in FIG. 5A) a second sweep over a plurality of MSEs may be conducted, and a second set of EM feedback-related values may be received, in operation 420. The second sweep may include substantially the same MSEs as the first sweep, or may include only a portion of the MSEs (e.g., a sub-set) of the first sweep.

The controller may be configured to identify changes between the first and the second sets by comparing a value received at each of the MSEs in the first set with a value received at the second set at the same MSE, in operation 430. The controller may choose to set the period of time between receiving the first and the second sets as a predetermined constant amount of time. Alternatively, the controller may set the period of time according to the EM feedback-related values or the identified change between the values of the first and second sets. For example, the controller may set the next period of time based on an average over all swept MSEs of the EM related-feedback values. In yet another option, the controller may be configured to continuously receive sets of EM feedback-values at a plurality of MSEs and identify the changes by determining the time derivative of the EM feedback-related value at each MSE. For example, the controller may calculate a difference between a first and second sets of: DR(MSEi), [DR(MSEi)]$^2$, $Z_{in}$[MSEi] or any other combinations of network parameters associated with a respective MSE. The controller may calculate or identify the difference by calculating or identifying time derivative between the sets (e.g., discrete derivative or continuous derivative), the derivative calculated may of the first order ($\partial/\partial t$) or of higher orders (e.g., $\partial/\partial t^2$). The controller may be configured to compare the determined time derivative (or any other time difference) with a first threshold value stored in a memory associated with the controller. The controller may further be configured to determine if the MSE is (or not) an object related MSE, based on the identified change. In some embodiments, for a particular MSE—if the changes between the values of the first and second sets (e.g., the time derivative) are larger than the first threshold, then the MSE may be considered an object related MSE. Otherwise, if the changes between the values of the first and second sets (e.g., the time derivatives) are smaller than the first threshold-the MSE may not be considered an object related MSE. In some embodiments, the first threshold value may be determined experimentally or according to simulations and calculations. In some embodiments, when no changes (or very small changes—e.g., below 1%, 2% or 5%—are detected)-it may indicate that the cavity is empty and thus energy application may be stopped. In some embodiments, the controller may further alert the host apparatus that the cavity is empty, e.g., by sending an alert signal to interface and/or displaying such alert on a display associated with the interface.

In some embodiments, method 400 may include setting a second threshold value and the controller may further compare the change in the EM feedback-related values at each MSE with the second threshold and adjust the RF energy application such that the RF energy is not applied at MSEs associated with EM feedback-related values having a change in the EM feedback-related values (e.g., time derivative) higher than the second threshold value, the second threshold value being higher than the first threshold value. For example, when rapid and discrete changes may occur in the the EM feedback-related values, due to a spark in the cavity (e.g., cavity 200) the controller may not apply RF energy at MSEs associated with the rapid and discrete changes. In some embodiments, the controller may further alert the host apparatus of such discrete changes, e.g., by sending an alert signal to interface and/or displaying such alert on a display associated with the interface.

In operation 440, the controller may adjust the RF energy application at two or more MSEs based on the identified change in the EM feedback-related value associated with the respective MSEs. Adjusting the RF energy application may include determining amounts of energy to be applied at two or more MSEs, for example, by determining a weight to be associated with each MSE. The weight may include an amount of RF energy to be applied at each MSE. For example, the weight may include a power level to be given to each MSE and/or the duration in which the RF energy may be applied to the energy application zone at the two or more MSEs. The controller may determine amounts of RF energy (weights) to be applied at two or more of the MSEs, based on the change in the EM feedback-related values associated with those MSEs. In some embodiments, the controller may adjust the RF energy application such that the RF energy is applied at MSEs associated with EM feedback related values having a time derivative higher than or lower than a threshold value.

Alternatively, the controller may be configured to determine the weight such that a direct relationship (e.g., a linear relationship) may be applied between the time derivative and the applied weight. The direct relationship may be of a general tendency, such that higher weight may be given to MSEs associated with higher time derivatives of the EM feedback values, and lower weights may be given to MSEs associated with lower time derivatives of the EM feedback values. The controller may further be configured to periodically adjust the RF energy application, for example, every 1 sec, 2 sec, etc. In operation 450, the controller may cause application of RF energy at one or more of the MSEs at the determined weights. For example, the controller may cause the application of RF energy only at object related MSEs at a constant weight. In yet another example, RF energy may be applied at object related MSEs in an amount inversely related to the EM related value received in the first or the second sets.

Figure 4B:
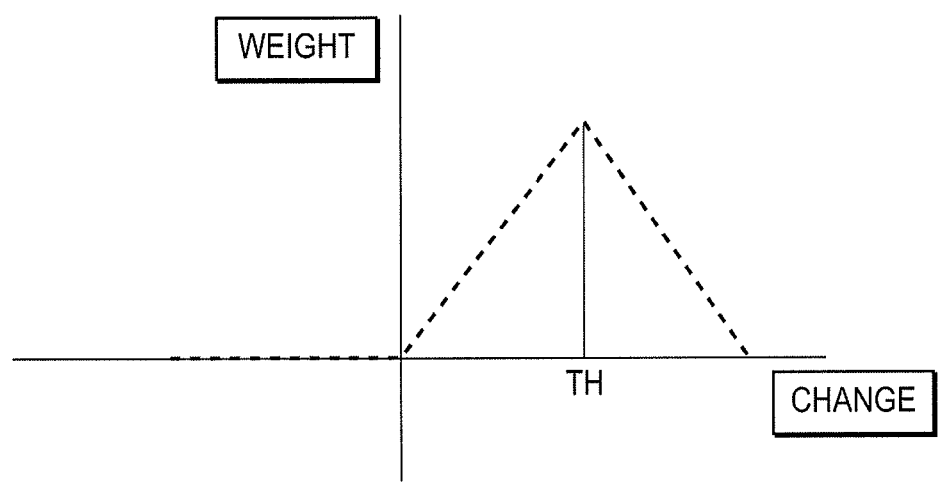
FIG. 4B is a graph presenting a function associating weights with values of changes over time in EM feedback related values, according to some embodiments of the invention.

In thawing applications, first the ice is thawed and as the heating continues, the water is heated which may decrease the value indicative of EM energy absorbable by the object (e.g., DR) as $\in$" of water decreases with temperature. MSEs in which the DR value decreases in time may indicate that the applied energy at this MSE is better absorbed in the water thus heating the water. Additionally, hot spots may correspond to high increase in the value indicative of EM energy absorbable by the object (e.g., DR). In some thawing applications, it may be desired to avoid applying energy at MSEs that are absorbed by water, thus avoiding over heating the water. Additionally or alternatively, it may be desired to avoid applying energy at MSEs that are associated with hot spots. In some embodiments (for example: in thawing applications), the controller may adjust energy application such that less weight or zero weight are associated with MSEs in which the EM feedback related values decrease over time. In some embodiments, the weight may be based on (e.g., a function of) the decrease rate—e.g., the higher the decrease rate—the lower the associated weight. In some embodiments, the controller may apply a linear function between the weight associated with an MSE and the identified change over time between two or more EM feedback related values at this MSE. FIG. 4B illustrates a graph presenting a function associating weights with values of changes over time in EM feedback related values, in accordance with some embodiments of the invention. As illustrated: if the value of the identified change is negative (i.e., the EM feedback related values decrease over time)—zero weight may be associated (i.e., no energy is applied); if the value of the identified change is positive and lower than a threshold—TH (i.e., the EM feedback related values increase over time at a first rate)—the associated weight may be directly (e.g., linearly) related to the value of the identified change—e.g., two times the value (weight=2*(change value)); if the value of the identified change is positive and higher than the threshold (TH) (i.e., the EM feedback related values increase over time at a second rate, higher than the first rate)—the associated weight may be inversely related to the value of the identified change—e.g., weight=b−a*(change value), where a and b are constants. In some embodiments, the associated weight may be zero if the value of the identified change is positive and higher than the threshold as this may indicate that this corresponds to hot-spot.

Figure 5A:
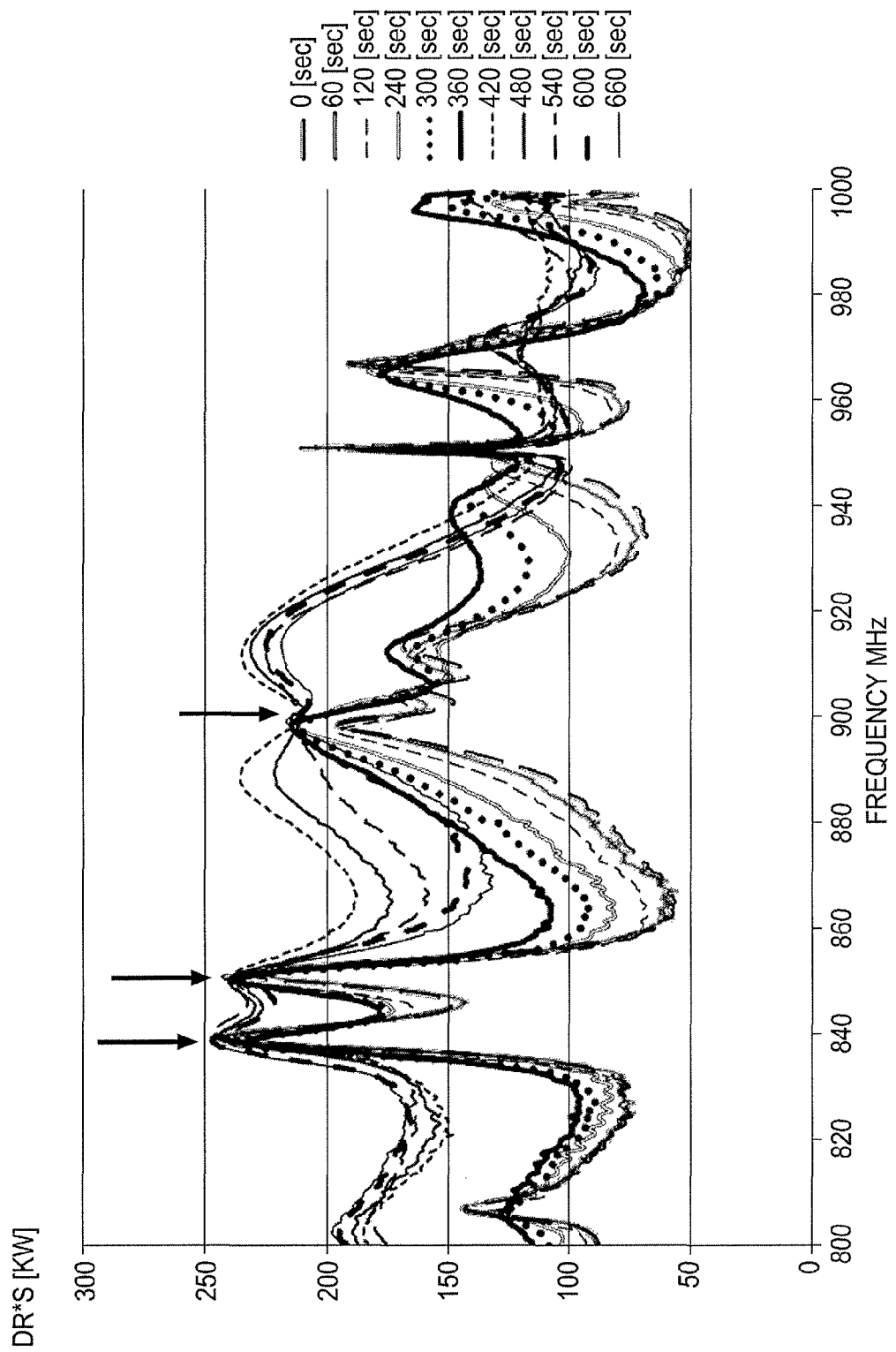
FIGS. 5A and 5B are graphs presenting results obtained from cooking experiments done in accordance with some embodiments of the invention.
Figure 5B:
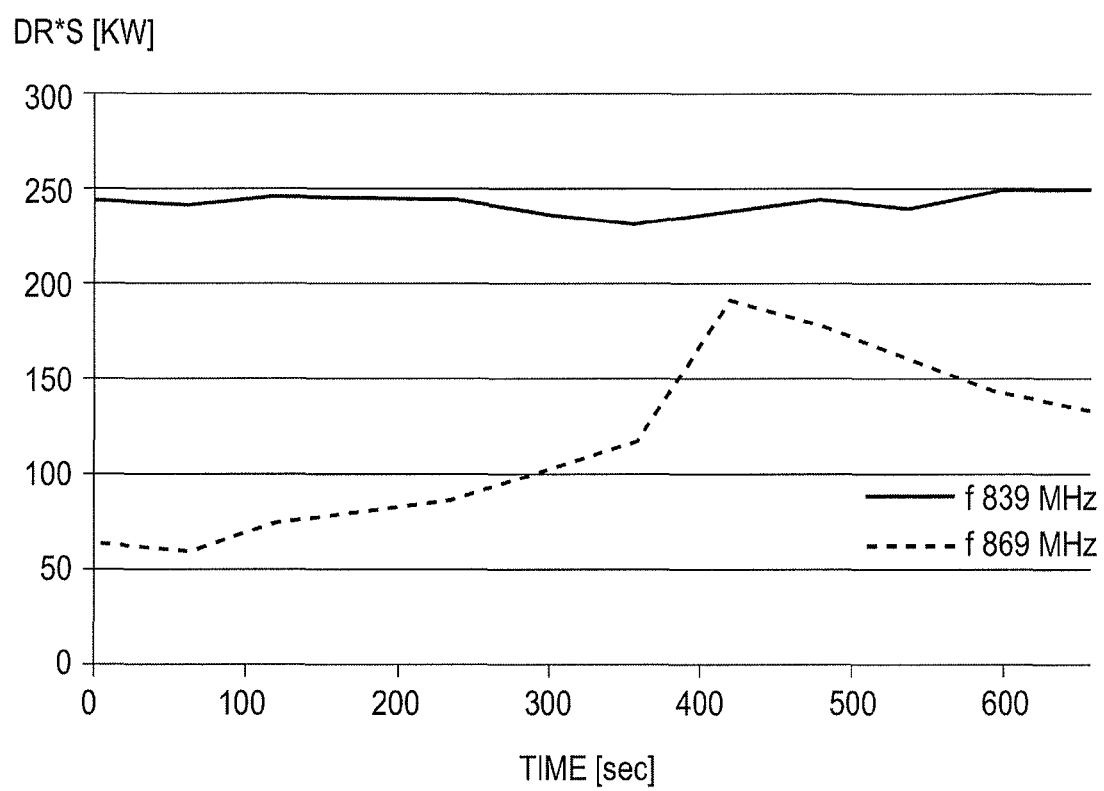

FIGS. 5A and 5B present results obtained in cooking experiments conducted in an experimental apparatus, operated according to some embodiments of the invention. Cooking experiments were conducted in an experimental apparatus for applying RF energy at a working frequency band of 800-1000 MHz and maximum power of 400 KW. In the experiment, beef was cooked by RF energy. FIG. 5A presents 11 curves of $P_A$, the power absorbed in the beef calculated by multiplying the DR with the supplied energy ($P_A = DR*P_S$) as a function of the frequency applied at various time periods. The various time periods and their respective line styles are listed next to the graphs. The vertical arrows mark frequencies associated with small changes in $P_A$ (e.g., below 10 KW (or 5%) per 60 seconds). Those frequencies may be regarded as 'cavity related frequencies'. All other frequencies in the band were associated with changes higher than 5% per 60 seconds, thus may be regarded as 'object related frequencies'.

FIG. 5B shows changes in time in the absorbed power calculated as above for two frequencies from the working band: 839 MHz (solid line) and 869 MHz (dashed line). At 839 MHz, very small changes between two consecutive measurements of $P_A$ of about 2.5% (approx 5 KW) are shown, thus 839 MHz may be regarded as a 'cavity related frequency'. At 869 MHz, larger changes between two consecutive measurements of $P_A$ of about 38% (approx 45 KW) are shown, thus 869 MHz may be regarded as an 'object related frequency'. In some embodiments, smaller amounts of RF energy (or none at all) may be applied at 839 MHz than at 869 MHz.

Figure 6:
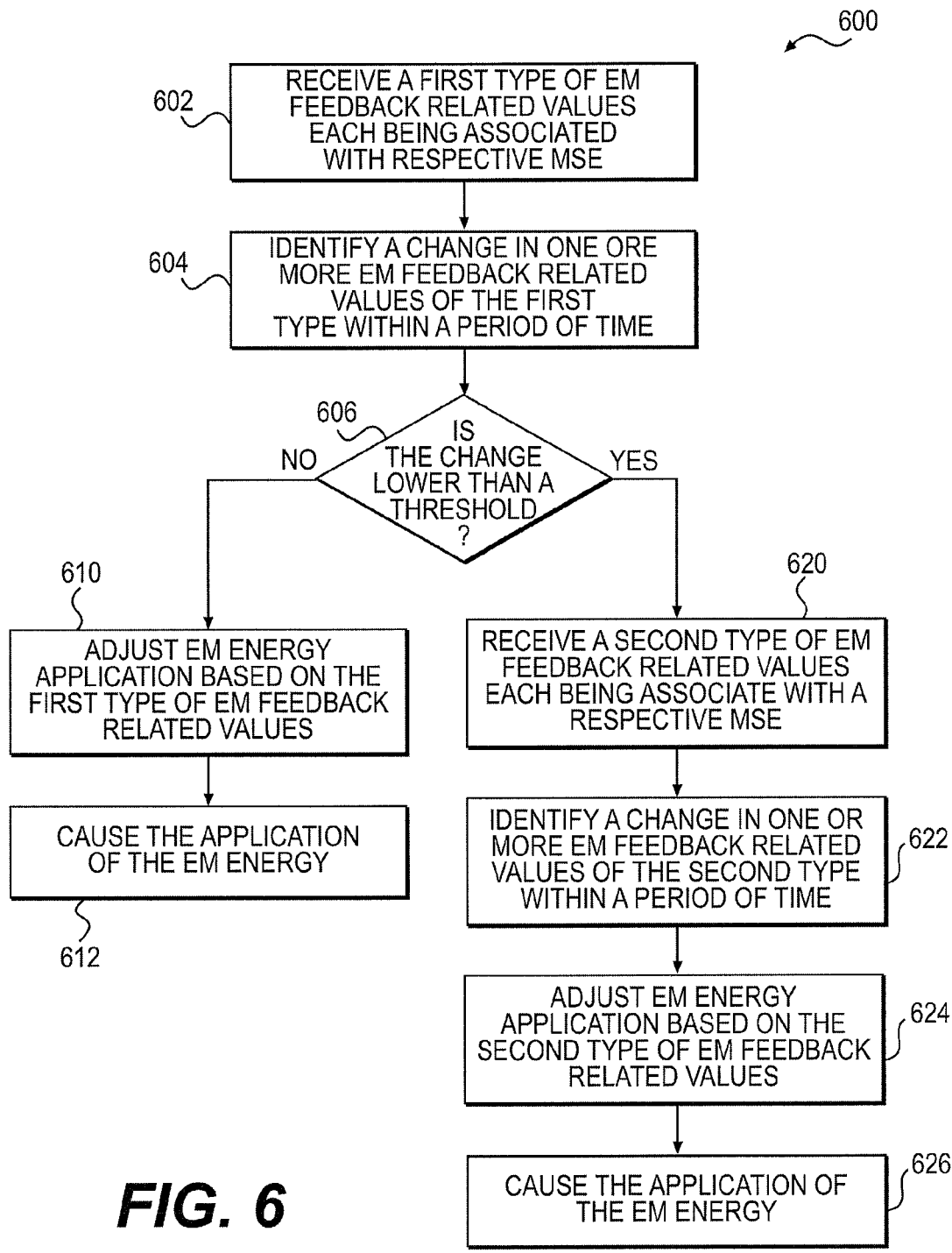
FIG. 6 is a flowchart of a method for adjusting RF energy application based on changes identified within a period of time in EM feedback related values, according to some embodiments of the invention.

Reference is made to FIG. 6, illustrating a method for adjusting RF energy application, according to some embodiments of the invention. Method 600 may be executed by a controller, for example, controller 150. In operation 602, the controller may receive a first type of EM feedback-related values each being associated with a respective MSE. Receiving the first type of MSE related EM feedback-related values may be conducted during a first sweep over at least some of the MSEs available in apparatus 100. The sweep may be conduct in a similar manner to the sweep disclosed with respect to operation 304, illustrated in method 300. The type of the EM feedback-related values may be for example: DR, average DR, $DR^2$, Zin, any one of the network parameters, any other values derivable from one or more (e.g., two) network parameters, or any other type of EM feedback-related values known in the art. Different types of EM-feedback related values may differ by the mathematical manipulation performed on the network parameters. Different types of EM-feedback related values may differ by the detected value-e.g., whether the complex value, the phase component or the magnitude components are detected. In an exemplary embodiment, a first set of 400 (four hundred) DR(MSEi) (wherein "i" is any number between 1-400) may be received by controller 150. The DR(MSEi) may be received as a result of RF energy application (e.g., a low amount of RF energy) to the energy application zone (e.g., when the Zone comprises an object) at the 400 MSEs and receiving from the energy application zone 400 DRs each being associated with a respective MSE.

Figure 8:
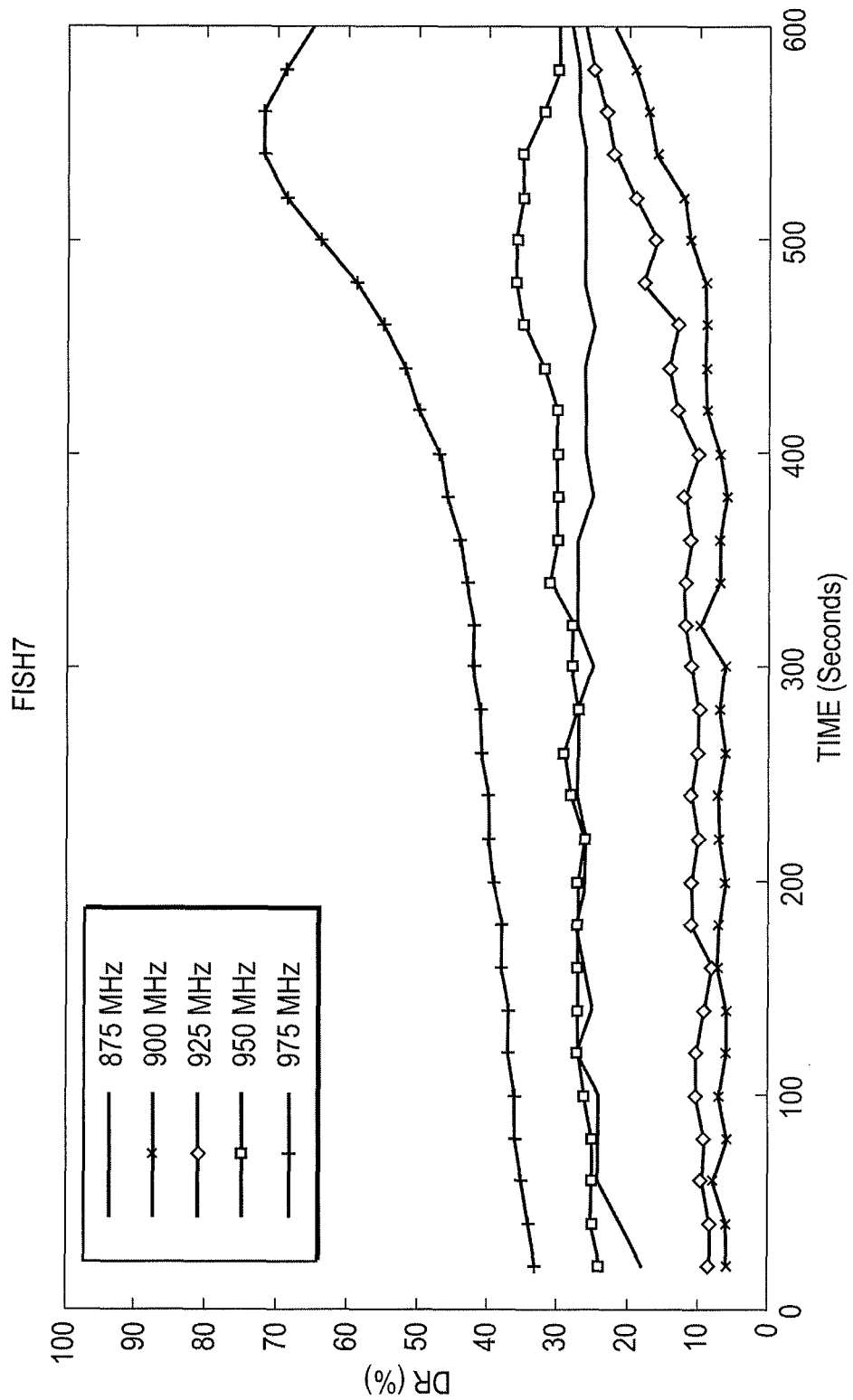
FIG. 8 is a graph presenting results obtained from thawing experiments done in accordance with some embodiments of the invention.

The controller may further identify a change in one or more EM feedback related values of the first type within a period of time, in operation 604. The change within a period of time may be detected by comparing two sets of EM feedback-related values of the first type, received at different times and calculating the difference between the two sets, for example, calculating a time derivative of the first type of EM feedback-related values at each MSE. In the exemplary embodiment, 400 time derivatives (or time differences) may be calculated for each of the DR(MSEi). In operation 606, the identified change (e.g., a time derivative of the DR(MSEi)) may be compared to a threshold value. Comparing the identified change to a threshold value may indicate if first type of EM feedback-related values is sensitive enough for detecting a change in the object, due to the RF energy application. For example, no significant change in DR values over time was detected during thawing of a frozen fish, as shown in FIG. 8. FIG. 8 presents measurements of DR values (presented in a percentage number) associated with a respective frequency over a period of 600 seconds. The frozen fish was thawed in an RF cooking oven working at 800-1000 MHz. During thawing of the fish, in the first 300 second, no significant change can be detected in the DR values at all the illustrated frequencies (875-975 MHz). In some embodiments, it may be concluded that DR values are not the best type of EM feedback-related values for detecting a change or small changes during a thawing of a fish.

If the change is lower than the threshold, operation 606-YES, the controller may receive (e.g., by detecting) a second type of EM feedback-related values, each being associated with a respective MSE, in operation 620. If the first type of EM feedback-related values is not sensitive enough for detecting changes in the EM feedback-related values during processing (e.g., thawing) with RF energy, it may be beneficiary to change the type of EM feedback-related values. For example, in thawing, if the DR is not sensitive enough for detecting a change during thawing of the fish, a Zin(MSEi) (input impedance) may be received. In some embodiments, Zin(MSEi) may be more sensitive to changes occurs in object during phase change, such as thawing.

After receiving the second type of EM feedback-related values, the controller may identify a change in one or more EM feedback related values of the second type within a period of time, in operation 622. For example, the controller may detect a time derivative of Zin(MSEi). The controller may further adjust the RF energy application at two or more MSEs based on the identified change in the second type of EM feedback related values, associated with the two or more MSEs within the period of time, in operation 624. The RF energy may be adjusted according to any method disclosed herein, for example, methods 300 and 400. The controller may adjust the RF energy by determining amounts of energy to be applied at the two or more MSEs based on the identified change in the EM feedback-related values, for example, by determining a weight for each MSE. The controller may further cause the application of the RF energy to the energy application zone, in operation 626.

If the change is higher than the threshold, operation 606-NO, the controller may adjust the RF energy application at two or more MSEs based on the identified change in the first type of EM feedback-related values, associated with the two or more MSEs within the period of time, in operation 610. The controller may adjust the RF energy application according to any method disclosed herein above. The controller may further cause the application of the RF energy to the energy application zone, in operation 612.

Switching between two types of EM-feedback related values (as described in exemplary method 600) may be used for processing application (e.g., when heating an object) or for sensing applications—e.g., when RF energy application is used for detecting a processing state of an object and/or a change in the processing state of the object.

Some embodiments, may be directed for applying RF energy to detect and/or sense one or more processing states (e.g., properties) of an object placed in an energy application zone to be processed (e.g., to be heated). The object may be processed by applying various types of energy, for example convection heating, infrared (IR) radiating (heating), etc. In addition to applying convection and/or IR heating, RF energy may be applied to process the object. Changes that may occur in properties of the object during processing may be referred to as a processing state of the object. Some examples of processing states of an object may include: a physical property of the object (e.g., temperature, pressure, flow rate, phase(s) etc.), chemical property of the object (e.g., pH, chemical composition, etc) and if the object is a food item—the processing state of an object may include: cooking and/or doneness state of the object (e.g., thawed, proofed, fully baked/cooked etc.). Changes in the object during processing may affect the dielectric behavior and response of the object to the RF energy application. One or more EM feedback-related values received from the energy application zone, optionally in response to an RF energy application, may be associated with one or more processing states of the object. The EM feedback-related values may be monitored during the processing of the object in order to detect the one or more processing states of the object.

In some embodiments, the association of with the EM feedback-related values may be determined before processing or detection begins. In some embodiments, the association may be determined based on simulations. In some embodiments, the association may be determined based on measurement, e.g., measurement performed using apparatus 100 and may be performed before the detection takes place (e.g., at a factory). An object to be processed may be placed in an RF energy application zone and may be processed either by RF energy and/or by any other energy source. During the energy application at least one indicator for the processing state of the object may be measured. An indicator of a processing state may include any measurements of a physical or chemical properties of the object either quantitatively (e.g., temperature, pressure etc.) or non-quantitatively (e.g., color, degree of doneness, taste, cooking state, etc.) of an object before, during or after processing of the object. The indication of the processing state may be measured (sensed) by a sensor (e.g., sensor 140) or may be determined through inspection by a user. Apparatus 100 may include a user interface (e.g., interface 160) configured to receive from a user an indication of the processing state of the object. During the processing and the detection of the processing state of the object, the EM feedback-related values each being associated with a respective MSE may be received and monitored over a period of time. For example, the controller may receive DR(MSEi) value every 0.5 sec during baking a pizza. The controller may than associate the processing state of the object, either measured or inspected, with the monitored EM feedback-related values. For example, sensor 140 may be a thermometer measuring the temperature in the center of the pizza during baking (e.g., every 0.5 sec) and controller 150 may associate the temperature measurements from the pizza with a change in DR(MSEi), for a particular MSEi, or for a subset of MSEs select. In some embodiments, the association between the processing state of the object and the monitored EM feedback-related values may be stored (e.g., in a memory associated with the apparatus-either provided in the apparatus or remotely accessible to the apparatus) for future use. Some exemplary methods for associating a processing state of the object may be found in International Patent Application No. PCT/US2012/053044 which is fully incorporated herein by reference.

Figure 7:
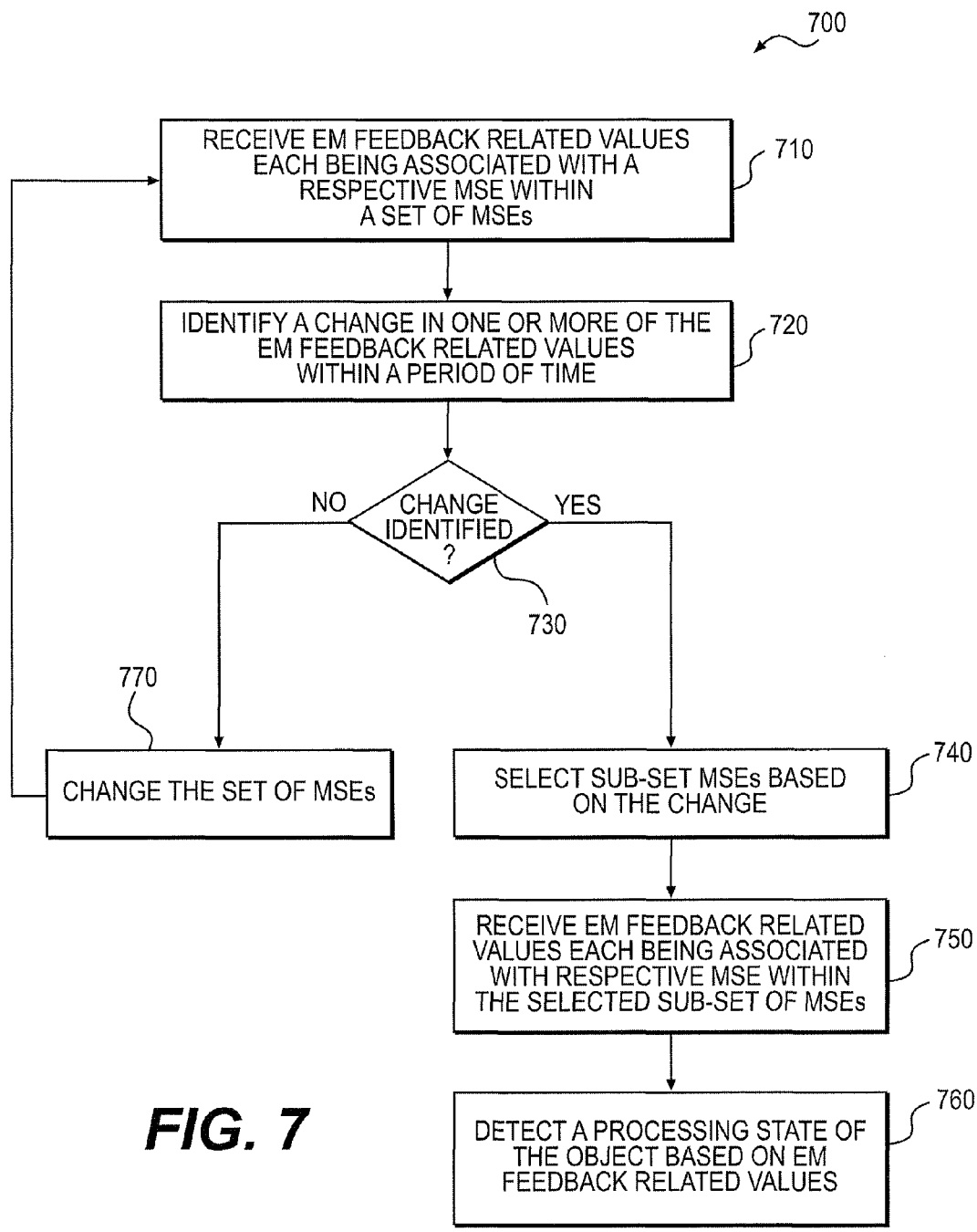
FIG. 7 is a flowchart of a method for selecting MSEs for detecting a processing state of an object, according to some embodiments of the invention.

Reference is made to FIG. 7 that illustrates a method for detecting a processing state of the object or a change in the processing state of the object, according to some embodiments of the invention. In order to detect a processing state of the object using EM feedback-related values, the change in the EM feedback-related values should be at least detectable and even easily detectable (e.g., higher than a threshold). As already shown and discussed above with respect to FIGS. 5A-5b and 8, not in all the MSEs (e.g., frequencies), changes in the EM feedback-related values are detectable. In some embodiments, a subset of MSEs may be selected from a plurality of MSEs such that the change in a period of time in EM feedback-related values associated with the MSEs included in the subset is detectable.

Method 700 may be executed by a controller, e.g., controller 150. The controller may receive electromagnetic (EM) feedback-related values from an energy application zone, each of the values being associated with a respective MSE included in a set of MSEs, in operation 710. The EM feedback-related values may be received in response to an application of low amount of RF energy (i.e., amounts that are insufficient for processing the object). The set of MSEs may include some or all the MSEs available in a certain apparatus (e.g., at least some of the frequencies and phases available in apparatus 100). The Object may be processed using any other form of energy, for example, IR radiation, convection heating, freezing, etc., or may be processed using RF energy, for example, using any method disclosed herein above. During the processing, at least one processing state (e.g., a property) of the object may change and may affect the dielectric properties of the object, thus may cause a change in the EM feedback-related values. The controller may identify the change in one or more of the EM feedback related values within a period of time, in operation 720. The change in the EM feedback related values may occur due the change in the dielectric properties of the object, due to processing. If a change has being identified, operation 730-YES, the controller in operation 740 may select subset of MSEs based on the change in the EM feedback related values identified. The subset selected may include all the MSEs associated with a change in one or more of the EM feedback-related values, within a period of time, higher than a threshold. For example, if the EM feedback related values are the Zin(MSEi) the subset may include all the MSEs that are associated with a time derivative of each Zin(MSEi) higher than a threshold. Other examples-may include selecting a sub-band of frequencies in which a change in the EM feedback-related values was detected (e.g., selecting sub-band of 50 MHz from available band of 200 MHz).

After selecting the subset of MSEs, the controller may receive EM feedback-related values at the selected sub-set of MSEs, in operation 750. A change in the received EM feedback-related values may be detectable, thus may allow the controller to detect the processing state of the object and/or a change in the processing state of the object based on the EM feedback-related values, wherein the EM feedback-related values are associated with the processing state of the object and/or the change in the processing state of the object, in operation 760. The detection may include comparing the EM feedback-related values with predetermined values (e.g., stored in a look-up table, or received by a tag—e.g., barcode or RFID tag, associated with the object) that associate EM feedback-related values with processing states of the object.

Receiving EM feedback related values only at a sub-set of MSEs may reduce the operation times, as less MSEs are swept (in operation 750). Alternatively and additionally, it may improve system efficiency as only MSEs which exhibit a change in corresponding EM feedback related values are swept for the detection. In some embodiments, every several cycles (e.g., once every 1 min, 2 min, after 50 heating cycles), the control may receive EM-feedback related values at the initial set of MSEs and not just the selected sub-set of MSEs (e.g., the available bandwidth) to check if the sub-set selection needs to be modified, e.g., whether it is required to re-select the sub-set (e.g., due to changes in the object).

If the change has not being identified, operation 730-NO, the controller in operation 770 may change the set of MSEs, for example, replace (i.e., change) a bandwidth of frequencies from 800-900 MHz to 900-1000 MHz and may repeat operation 710, until indentifying the change.

In the foregoing, various features are grouped together in a single embodiment for purposes of streamlining the disclosure. This method of disclosure is not to be interpreted as reflecting an intention that the claims require more features than are expressly recited in each claim. Rather, as the following claims reflect, inventive aspects lie in less than all features of a single foregoing disclosed embodiment.

Thus, the following claims are hereby incorporated into this Description of the Exemplary Embodiments, with each claim standing on its own as a separate embodiment.

Thus, it is intended that the specification and examples be considered as exemplary only, with a true scope of the present disclosure being indicated by the following claims and their equivalents.

What is claimed is:

1. A method of processing an object in a cavity by applying radio frequency (RF) energy to the cavity, the method comprising applying RF energy to the cavity at a plurality of frequencies, and
for each frequency:
receiving a value indicative of a dielectric response of the cavity to RF energy applied;
identifying a change over time in the value indicative of the dielectric response of the cavity to RF energy; and
adjusting the RF energy application based on the identified change,
wherein adjusting the RF energy application based on the identified change comprises applying more energy at a first plurality of frequencies than at a second plurality of frequencies, wherein the change over time identified for the first plurality of frequencies is higher than a first threshold and the change over time identified for the second plurality of frequencies is lower than the first threshold.

2. The method of claim 1, wherein less energy is applied at frequencies for which the identified change over time is larger than a second threshold than at frequencies for which the identified change over time is between the first threshold and the second threshold, and the second threshold is higher than the first threshold.

3. The method of claim 1, wherein less energy is applied at frequencies for which a non-continuous change over time is identified than at frequencies for which a change larger than the first threshold is identified.

4. The method of claim 1, wherein adjusting the RF energy application at a certain frequency comprises adjusting a power level at which RF energy is applied at the certain frequency.

5. The method of claim 1, wherein adjusting the RF energy application at a certain frequency comprises adjusting a duration for which RF energy is applied at the certain frequency.

6. A method of processing an object in a cavity by applying radio frequency (RF) energy to the cavity, the method comprising applying RF energy to the cavity at a plurality of frequencies, and
for each frequency:
receiving a value indicative of a dielectric response of the cavity to RF energy applied;
identifying a change over time in the value indicative of the dielectric response of the cavity to RF energy; and
adjusting the RF energy application based on the identified change,
wherein identifying a change over time in one or more of the values for each frequency comprises:
receiving a first set of values at a first time, each value of the first set of values corresponds to the dielectric response of the cavity at one of the frequencies at a first time,
receiving a second set of values at a second time, each value of the second set of values corresponds to the dielectric response of the cavity at one of the frequencies at a second time, and
comparing the first set of values with the second set of values.

7. The method of claim 1, wherein the value indicative of a dielectric response of the cavity to RF energy is a network parameter.

8. The method of claim 1, wherein the value indicative of a dielectric response of the cavity to RF energy is derivable from one or more network parameters.

9. An apparatus for processing an object in a cavity by applying radio frequency (RF) energy to the cavity, the apparatus comprising:
a source of RF energy;
an antenna configured to feed RF energy from the source to the cavity; and
a controller configured to control the source to apply RF energy to the cavity via the antenna at a plurality of frequencies, wherein the controller is programmed to:
identify for each of the plurality of frequencies a change over time in a value indicative of the dielectric response of the cavity to RF energy applied at the each of the plurality of frequencies; and
adjust the RF energy application at the each of the plurality of frequencies based on the identified change,
wherein the controller is programmed to adjust the RF energy application based on the identified change by applying more energy at a first plurality of frequencies than at a second plurality of frequencies, wherein the change over time identified for the first plurality of frequencies is higher than a first threshold and the change over time identified for the second plurality of frequencies is lower than the first threshold.

10. The apparatus of claim 9, wherein the controller is programmed to adjust the RF energy application based on the identified change by applying less energy at frequencies for which the identified change over time is larger than a second threshold than at frequencies for which the identified change over time is between the first threshold and the second threshold, and the second threshold is higher than the first threshold.

11. The apparatus of claim 9, wherein the controller is programmed to adjust the RF energy application based on the identified change by applying less energy at frequencies for which a non-continuous change over time is identified than at frequencies for which a change larger than the first threshold is identified.

12. The apparatus of claim 9, wherein the controller is programmed to adjust the RF energy application by adjusting at least a power level at which RF energy is applied.

13. The apparatus of claim 9, wherein the controller is programmed to adjust the RF energy application by adjusting at least a duration for which RF energy is applied.

14. The apparatus of claim 9, wherein the value indicative of a dielectric response of the cavity to RF energy comprises a network parameter.

15. The apparatus of claim 9, wherein the value indicative of a dielectric response of the cavity to RF energy is derivable from one or more network parameters.

* * * * *